(12) United States Patent
Weterings et al.

(10) Patent No.: US 9,181,532 B2
(45) Date of Patent: *Nov. 10, 2015

(54) PRODUCTION OF GALACTOSYLATED N-GLYCANS IN PLANTS

(75) Inventors: Koen Weterings, Raleigh, NC (US); Sylvie Van Herrewege, Deinze (BE)

(73) Assignee: Icon Genetics GmbH (DE)

(*) Notice: Subject to any disclaimer, the term of this patent is extended or adjusted under 35 U.S.C. 154(b) by 485 days.

This patent is subject to a terminal disclaimer.

(21) Appl. No.: 13/560,148

(22) Filed: Jul. 27, 2012

(65) Prior Publication Data

US 2013/0052683 A1 Feb. 28, 2013

Related U.S. Application Data

(60) Provisional application No. 61/513,107, filed on Jul. 29, 2011.

(30) Foreign Application Priority Data

Aug. 1, 2011 (EP) .................................. 11075181

(51) Int. Cl.
*C12N 15/62* (2006.01)
*C12N 15/54* (2006.01)
*A61K 38/45* (2006.01)
*C12N 9/10* (2006.01)
*C12N 15/82* (2006.01)

(52) U.S. Cl.
CPC .......... *C12N 9/1051* (2013.01); *C12N 15/8258* (2013.01); *C07K 2319/01* (2013.01); *C07K 2319/05* (2013.01)

(58) Field of Classification Search
None
See application file for complete search history.

(56) References Cited

FOREIGN PATENT DOCUMENTS

| WO | 03078637 A2 | 9/2003 |
| WO | 2008125972 A2 | 10/2008 |
| WO | 2008141806 A1 | 11/2008 |
| WO | 2008151440 A1 | 12/2008 |
| WO | 2010121818 A1 | 10/2010 |

OTHER PUBLICATIONS

Strasser et al (JBC, 284, pp. 20479-20485, 2009).*
GenBank NM_001016664.2 (published Nov. 2006; see sequence appended to the action).*
Boevink et al (Plant J. 15(3), pp. 441-447, 1998).*
GenBank NM_001113344.1 (published Jan. 2008; see sequence appended to the action).*
Lau et al (Biotechnology Advances, 27, pp. 1015-1022, 2009).*
Extended European Search Report for Application No. EP12005512 dated Jan. 22, 2013.
Frey Alexander D et al., "Expression of rat beta(1,4)-N-acetylglucosaminyltransferase III in Nicotiana tabacum remodels the plant-specific N-glycosylation.", Plant Biotechnology Journal Jan. 2009, vol. 7, No. 1, Jan. 2009, pp. 33-48, XP002689787.
Joshi L et al., "Bioprospecting in plants for engineered proteins", Current Opinion in Plant Biology, Quadrant Subscription Services, GB, vol. 8, No. 2, Apr. 1, 2005, pp. 223-226, XP027848146.
Strasser et al, "Generation of glyco-engineered Nicotiana benthamiana for the production of monoclonal antibodies with a homogeneous human-likeN-glycan structure", Plant Biotechnology Journal, Blackwell, Oxford, GB, vol. 6, No. 4, May 1, 2008, pp. 392-402, XP009104007.
Strasser et al, "Improved Virus Neutralization by Plant-produced Anti-HIV Antibodies with a Homogeneous beta 1,4-Galactosylated N-Glycan Profile", Journal of Biolog ical Chemistry, vol. 284, No. 31, Jul. 2009, pp. 20479-20485, XP002689786.

* cited by examiner

*Primary Examiner* — David T Fox
*Assistant Examiner* — Stephen Uyeno
(74) *Attorney, Agent, or Firm* — Lerner, David, Littenberg, Krumholz & Mentlik, LLP

(57) ABSTRACT

The invention provides methods for increasing the levels of bi-antennary mono- and fully galactosylated N-glycans, and for decreasing the levels of hybrid-type galactosylated N-glycans on glycoproteins produced in plants or plant cells. In addition, the invention provides methods for the production of heterologous glycoproteins with increased levels of bi-antennary mono- and fully galactosylated N-glycans, or decreased levels of hybrid-type galactosylated N-glycans in plants or plant cells.

16 Claims, 7 Drawing Sheets

PRODUCTION OF GALACTOSYLATED N-GLYCANS IN PLANTS

CROSS-REFERENCE TO RELATED PATENT APPLICATIONS

The present application claims the benefit of the filing date of U.S. Provisional Patent Application No. 61/513,107, filed Jul. 29, 2011, and European Patent Application No. 11 075 181.5, filed Aug. 1, 2011, the disclosures of which are hereby incorporated herein by reference.

FIELD OF THE INVENTION

The current invention relates to the field of molecular farming, i.e., the use of plants and plant cells as bioreactors to produce peptides and proteins, including biopharmaceuticals, particularly polypeptides and proteins with pharmaceutical interest such as therapeutic proteins, which have an N-glycosylation pattern that improves their efficacy, in particular galactosylated N-glycan structures. The invention may also be applied to alter the glycosylation pattern of proteins in plants for any purpose, including modulating the activity or half-life of endogenous plant proteins or proteins introduced in plant cells.

BACKGROUND

Glycosylation is the covalent linkage of an oligosaccharide chain to a protein resulting in a glycoprotein. In many glycoproteins, the oligosaccharide chain is attached to the amide nitrogen of an asparagine (Asn) residue and leads to N-glycosylation. Glycosylation represents the most widespread post-translational modification found in natural and biopharmaceutical proteins. For example, more than half of the human proteins are glycosylated and their function frequently depends on particular glycoforms (glycans), which can affect their plasma half life, tissue targeting or even their biological activity. Similarly, more than one-third of approved biopharmaceuticals are glycoproteins and both their function and efficiency are affected by the presence and composition of their N-glycans. The functional activity of therapeutic glycoproteins is also frequently dependent on their glycosylation; this can be the case, for example in blood factors, antibodies and interferons. This requirement for glycosylation explains why many biopharmaceuticals are produced in expression systems with N-glycosylation capability. In recent years plants have emerged as an attractive system for the production of therapeutic proteins, as plants are generally considered to have several advantages, including the lack of animal pathogens such as prions and viruses, low cost and the large-scale production of safe and biologically active valuable recombinant proteins, the case of scale-up, efficient harvesting and storage possibilities. However, N-linked glycans from plants differ in many aspects from those of mammalian cells. In plants, beta(1,2)-xylose and alfa(1,3)-fucose residues have been shown to be linked to the core Man3GlucNAc2-Asn of glycans, whereas they are not detected on mammalian glycans, where sialic acid residues and terminal beta(1,4)-galactosyl structures occur instead. The unique N-glycans added by plants could impact both immunogenicity and functional activity of the protein and, consequently, may represent a limitation for plants to be used as a protein production platform. Indeed, the immunogenicity of beta(1,2)-xylose residues and alfa(1,3)-fucose in mammals has been described (Bardor et. al., 2003, Glycobiology 13: 427). Glyco-engineering with the combined knock-out/knock-in approach of glycosylation-related enzyme genes has been recognized for the avoidance of plant-specific glycan residues as well as the introduction of human glycosylation machinery in plants.

Beta(1,4)-galactose has been introduced in plants by expression of human beta(1,4)-galactosyltransferase I (GalT) (Bakker et. al., 2001, Proc. Natl. Acad. Sci. USA 98: 2899), and chicken and zebrafish beta(1,4)-galactosyltransferase I (WO2008/125972). In several studies, the GalT enzyme was fused to a golgi targeting signal as to alter the localization in Golgi and to improve GalT activity. Bakker et. al. (2006, Proc. Natl. Acad. Sci. USA 103: 7577) and WO2003/078637 describe a fusion of human GalT to the cytoplasmic tail, transmembrane domain, and stem region (CTS domain) of *Arabidopsis thaliana* xylosyltransferase (XylT). They found that, in tobacco, addition of this CTS domain caused a sharp reduction of N-glycans with core-bound xylose and fucose residues. Vezina et. al. (2009, Plant. Biotechnol. J. 7: 442) and WO2008/151440 fused GalT to the membrane anchorage domain of the N-acetylglucosaminyltransferase I (GNTI) from tobacco, in order to allocate GalT activity in the early plant secretory pathway. Glycans from the *N. benthamiana* plants expressing the GNTI-GalT fusion comprised galactosylated and non-galactosylated hybrids and immature oligomannose N-glycans, and contained no detectable alfa(1,3)-fucose and beta(1,2)-xylose residues. WO2008/125972 replaced the chicken and zebrafish CTS domain with the CTS of rat sialyltransferase. The zebrafish GalT having substituted its amino-terminal for the CTS region of rat sialyltransferase, produced mainly biantennary, double galactosylated N-glycans in *Nicotiana benthamiana*. Strasser et. al. (2009, J. Biol. Chem. 284: 20479) fused human GalT to the rat sialyltransferase CTS domain. This fusion protein was expressed in *N. benthamiana* which lacks plant-specific beta(1,2)-xylosyltransferase and core alfa(1,3)-fucosyltransferase activities and expresses anti-human immunodeficiency virus antibody. The predominant glycoform of the expressed antibodies was the fully galactosylated AA structure, and to some extent incompletely processed and monoantennary galactosylated structures were present. Galactosylated structures represented about 80% of all glycoforms. Moreover, it was observed that the antigen-binding of these plant-derived antibodies was 115-140% as compared to CHO-derived antibodies. Importantly, the fully galactosylated plant-derived antibodies neutralized HIV more efficiently than other glycoforms from plant and CHO cells.

The current invention provides methods and means to improve production of bi-antennary beta(1,4)-galactosylated N-glycan structures and to reduce the production of hybrid-type beta(1,4)-galactosylated N-glycans on glycoproteins in plants and plant cells, as will become apparent from the following description, examples, drawings and claims provided herein.

SUMMARY OF THE INVENTION

In a first embodiment, the invention provides a method to increase levels of glycosylation of glycoproteins produced in a plant or plant cell comprising the steps of providing a plant cell with a chimeric gene comprising a plant-expressible promoter, a DNA region encoding a CTS domain operably linked to the stem region and the catalytic domain of a glycosyltransferase, and a DNA region involved in transcription termination and polyadenylation, cultivating said plant cell and isolating beta(1,4)-galactosylated glycoproteins from said plant cell.

It is another object of the invention to provide a method to increase levels of bi-antennary N-glycans comprising at least one beta(1,4)-galactose residue on glycoproteins produced in a plant or plant cell comprising the steps of providing a plant cell with a chimeric gene comprising a plant-expressible promoter, a DNA region encoding a CTS domain operably linked to the stem region and the catalytic domain of a beta(1,4)-galactosyltransferase, and a DNA region involved in transcription termination and polyadenylation, and cultivating said plant cell and isolating beta(1,4)-galactosylated glycoproteins from said plant cell. In another embodiment of the invention, a method is provided to decrease the levels of hybrid-type beta(1,4)-galactosylated protein-bound glycans. In another object of the invention, said CTS domain is a CTS domain known to target proteins to the trans-golgi compartment. In yet another object, said CTS domain is the CTS domain of rat alfa(2,6)-sialyltransferase. In a particular embodiment, said beta(1,4)-galactosyltransferase is the *Xenopus tropicalis* beta(1,4)-galactosyltransferase.

In another embodiment of the invention, said DNA region encodes the polypeptide comprising at least 90% similarity to SEQ ID NO:3 and, in another embodiment, said DNA region comprises at least 90% sequence identity to SEQ ID NO:2.

It is another object to provide a method to increase levels of beta(1,4)-galactosylation on protein-bound N-glycans produced in a plant or plant cell having reduced beta(1,2)-xylosyltransferase and reduced alfa(1,3)-fucosyltransferase activity.

In another object of the invention, a method is provided to increase levels of beta(1,4)-galactosylation on a heterologous glycoprotein produced in a plant or plant cell expressing a heterologous glycoprotein. In yet another embodiment, the method further comprises purification of said heterologous protein.

Another embodiment of the invention is a glycoprotein, such as a beta(1,4)-galactosylated glycoprotein, obtained by the methods according to the invention.

In another embodiment, a plant or plant cell is provided comprising a chimeric gene comprising a plant-expressible promoter, a DNA region encoding a CTS domain operably linked to the stem region and the catalytic domain of the *Xenopus tropicalis* beta(1,4)-galactosyltransferase, and a DNA region involved in transcription termination and polyadenylation. In yet another embodiment, said plant or plant cell has reduced beta(1,2)-xylosyltransferase activity and reduced alfa(1,3)-fucosyltransferase activity. In yet another embodiment, said plant or plant cell comprises a heterologous glycoprotein which is expressed in said plant or plant cell from a chimeric gene comprising a plant expressible promoter and a DNA region encoding said heterologous glycoprotein.

In another embodiment, a chimeric gene is provided comprising a plant-expressible promoter, a DNA region encoding a CTS domain operably linked to the stem region and the catalytic domain of the *Xenopus tropicalis* beta(1,4)-galactosyltransferase, and a DNA region involved in transcription termination and polyadenylation.

In yet a further aspect the beta(1,4)-galactosyltransferase comprising a duplicated stem region are used to obtain glycoproteins having bi-antennary N-glycans comprising at least one terminal beta(1,4)-galactose residue in plants or plant cells for the production of heterologous proteins.

DETAILED DESCRIPTION OF DIFFERENT EMBODIMENTS OF THE INVENTION

Figure 1:
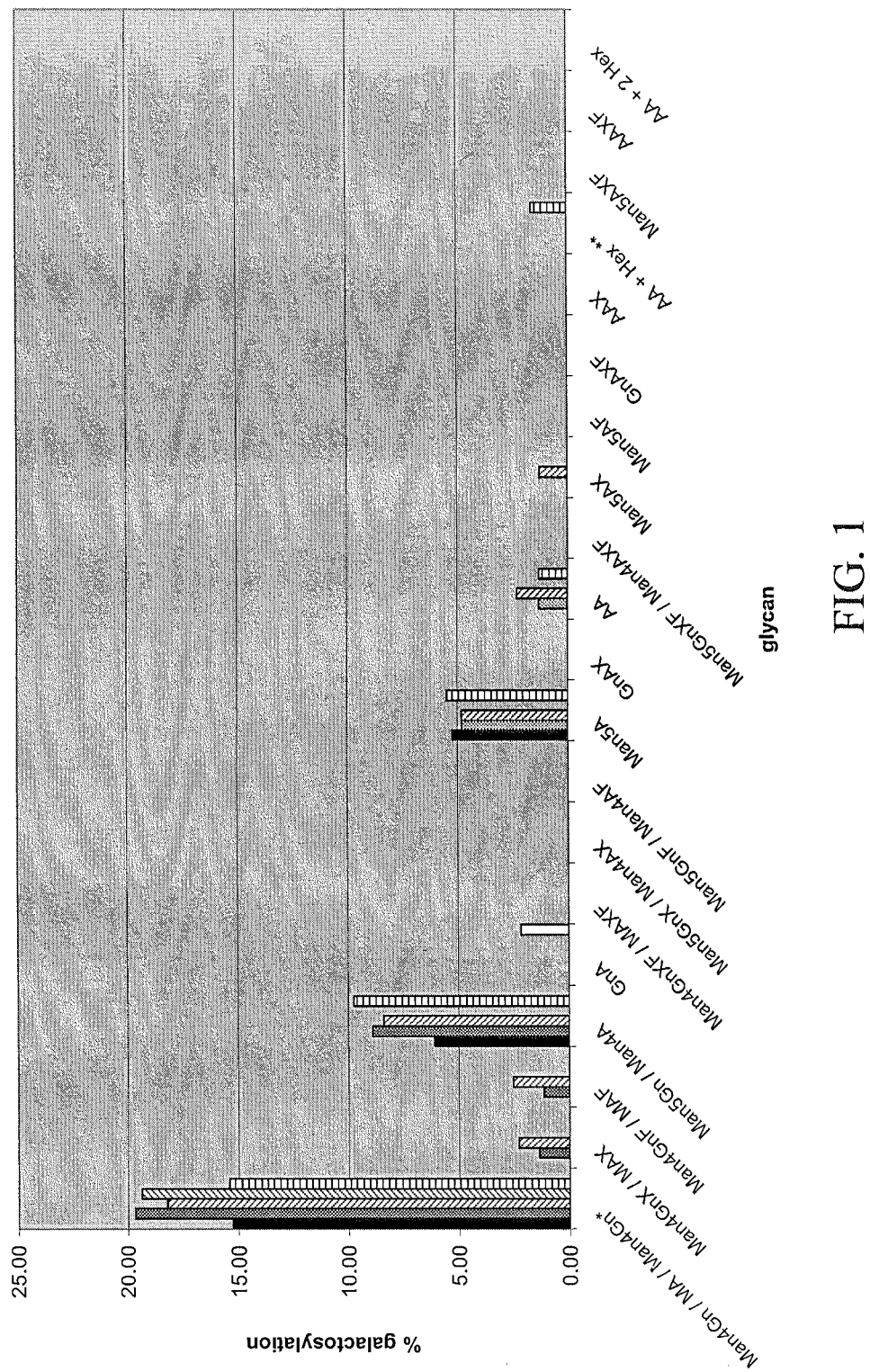
FIG. 1: MALDI-TOF MS analysis of endogenous glycosylated proteins in a xylosyltransferase negative and fucosyltransferase negative (XylT/FucT RNAi) background of *Nicotiana benthamiana* expressing ST(CTS)-XtGalT(SCAT). 6302 (black bars), 6303 (hatched bars), 6305 (diagonally striped bars top left to bottom right), 6309 (diagonally striped bars bottom left to top right) and 6315 (horizontally striped bars) are different transgenic lines expressing ST(CTS)-XtGalT(SCAT); white bars represent the XylT/FucT RNAi line not expressing ST(CTS)-XtGalT(SCAT).

The current invention is based on the observation that duplication of the stem region or a substantial part thereof in a chimeric beta(1,4)-galactosyltransferase results in increased levels of bi-antennary mono- and fully galactosylated N-glycans and decreased hybrid-type galactosylated N-glycans on glycoproteins produced in plant cells.

In a first embodiment, the invention provides a method to increase levels of glycosylation of glycoproteins produced in a plant or plant cell comprising the steps of providing a plant cell with a chimeric gene comprising a plant-expressible promoter, a DNA region encoding a CTS domain operably linked to the stem region and the catalytic domain of a glycosyltransferase, and a DNA region involved in transcription termination and polyadenylation, cultivating said plant cell and isolating beta(1,4)-galactosylated glycoproteins from said plant cell.

"Increased levels" is meant to be an increase with respect to levels as obtained in isogenic plants comprising a galactosyltransferase with one stem region only. Said increase can be an increase of at least 5%, or of at least 10%, or at least 15%, or at least 20%, or at least 30%, or at least 40%, or at least 50%, or at least 60%, or at least 70%, or at least 80%, or at least 90%, or an even higher increase. The amount of glycosylated glycan structures associated with a produced glycoprotein can be determined according to the methods described in this application.

Increased levels of glycosylation can consist of an increased level of glycan structures on glycoproteins, or an increased level of specific glycan structures on glycoproteins, or an increased level of glycan structures and increased level of specific glycan structures on glycoproteins. The increased level of specific glycan structures can, for example, be an increase in the level of glycan structures lacking beta(1,2)-xylose residues, or an increase in the level of glycan structures lacking alfa(1,3)-fucose residues, or an increase in the level of glycan structures having terminal beta(1,4)-galactose residues, or an increase in the level of glycan structures having terminal alfa(2,3) or alfa(2,6)-sialic acid residues, or an increase in multi-antennary glycan structures, or any combination thereof.

In another embodiment, the invention provides a method to increase levels of bi-antennary N-glycans comprising at least one terminal beta(1,4)-galactose residue on glycoproteins produced in a plant or plant cell comprising the steps of providing a plant cell with a chimeric gene comprising a plant-expressible promoter, a DNA region encoding a CTS domain operably linked to the stem region and the catalytic domain of a beta(1,4)-galactosyltransferase, and a DNA region involved in transcription termination and polyadenylation, cultivating said plant cell and isolating beta(1,4)-galactosylated glycoproteins from said plant cell.

Increased levels of bi-antennary N-glycans comprising at least one terminal beta(1,4)-galactose residue can be an increase in the abundance of mono-galactosylated structures such as MA or GnA, or can be an increase in the abundance of the fully galactosylated AA structure, or can be an increase in the abundance of GnA and AA structures.

"Bi-antennary N-glycans" as used herein refers to non-hybrid bi-antennary glycans. Nomenclature of the glycan structures is the nomenclature as proposed by the Consortium for Functional Glycomics. AA refers to a bi-antennary glycan having two terminal Galactose residues. MA refers to a bi-antennary glycan having one terminal Mannose residue, and one terminal Galactose residue. GnA refers to a bi-antennary glycan having one terminal N-acetylglucosamine residue, and one terminal Galactose residue.

As used herein "a plant cell" is a cell of a higher plant belonging to the Angiospermae or the Gymospermae, but a plant cell can also be a lower plant cell such as plant cells belonging to Algae and Bryophyta. The higher plant cell can, for example, be a cell of a plant belonging to the Brassicaceae or the Solanaceae, including *Arabidopsis* or *Nicotiana* spp.

"Beta(1,4)-galactosyltransferase", also "β(1,4)-galactosyltransferase", or "beta(1,4)-GalT", or "GalT" refers to the glycosyltransferase EC 2.4.1.38. Beta(1,4)-galactosyltransferases are trans-Golgi glycosyltransferases with a type II membrane protein topology, a short N-terminal cytoplasmic domain, a membrane-spanning region, as well as a stem and a C-terminal catalytic domain facing the trans-Golgi-lumen. The beta(1,4)-galactosyltransferase transfers galactose from uridine-diphosphate-D-galactose (UDP-Gal) to an acceptor sugar molecule generating a beta(1,4) linkage between galactose and the acceptor sugar. The family of beta(1,4)-galactosyltransferases (GalT) comprises at least seven members.

Genes encoding GalT are well known and include the following database (National Centre for Biotechnology Information (NCBI) or GenBank) accession numbers identifying experimentally demonstrated and putative GalT cDNA and gene sequences, parts thereof or homologous sequences: *Homo sapiens*: X55415, NM 004776 or NM 001497; *Gallus gallus*: NM_205202; *Danio rerio* (zebrafish): FJ829869; *Bos taurus*: NM 177512; *Mus musculus*: NM_022305 or NM146045; *Tetraodon nigroviridis*: CAAE01013769. Genes encoding GalT can also be designed based on GalT protein sequences such as, for example, the GalT protein from *Xenopus tropicalis* (NP_001016664).

Based on the available sequences, the skilled person can isolate genes encoding beta(1,4)-galactosyltransferase other than the genes mentioned above. Homologous nucleotide sequence may be identified and isolated by hybridization under stringent conditions using as probes identified nucleotide sequences.

"Stringent hybridization conditions" as used herein means that hybridization will generally occur if there is at least 95% and preferably at least 97% sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared carrier DNA such as salmon sperm DNA, followed by washing the hybridization support in 0.1×SSC at approximately 65° C., preferably twice for about 10 minutes. Other hybridization and wash conditions are well known and are exemplified in Sambrook et. al., Molecular Cloning: A Laboratory Manual, Second Edition, Cold Spring Harbor, N.Y. (1989), particularly chapter 11.

Other sequences encoding beta(1,4)-galactosyltransferases may also be obtained by DNA amplification using oligonucleotides specific for genes encoding beta(1,4)-galactosyltransferases as primers, such as but not limited to oligonucleotides comprising or consisting of about 20 to about 50 consecutive nucleotides from the known nucleotide sequences or their complement.

Other sequences encoding beta(1,4)-galactosyltransferases may also be obtained by searching nucleotide and protein databases for sequences homologous to any of the known beta(1,4)-galactosyltransferases. Methods to search sequence databases are well known in the art such as, for example, Basic Local Alignment Search Tool (BLAST). Examples of sequence databases are NCBI or GenBank.

Obtained nucleotide sequences of genes encoding beta(1,4)-galactosyltransferase should be verified for encoding a polypeptide having an amino acid sequence which is at least 60%, 65%, 70%, 75%, 80%, 85%, 90% or 95% identical to a known beta(1,4)-galactosyltransferase.

As used herein, the term "plant-expressible promoter" means a DNA sequence that is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S (Harpster et. al. (1988) *Mol Gen Genet.* 212(1): 182-90, the subterranean clover virus promoter No 4 or No 7 (WO9606932), or T-DNA gene promoters but also tissue-specific or organ-specific promoters including but not limited to seed-specific promoters (e.g., WO89/03887), organ-primordia specific promoters (An et. al. (1996) *Plant Cell* 8(1): 15-30), stem-specific promoters (Keller et. al., (1988) *EMBO J.* 7(12): 3625-3633), leaf specific promoters (Hudspeth et. al. (1989) *Plant Mol Biol.* 12: 579-589), mesophyl-specific promoters (such as the light-inducible Rubisco promoters), root-specific promoters (Keller et. al. (1989) *Genes Dev.* 3: 1639-1646), tuber-specific promoters (Keil et. al. (1989) *EMBO J.* 8(5): 1323-1330), vascular tissue specific promoters (Peleman et. al. (1989) *Gene* 84: 359-369), stamen-selective promoters (WO 89/10396, WO 92/13956), dehiscence zone specific promoters (WO 97/13865) and the like.

A "transcription termination and polyadenylation region" as used herein is a sequence that drives the cleavage of the nascent RNA, whereafter a poly(A) tail is added at the resulting RNA 3' end, functional in plants. Transcription termination and polyadenylation signals functional in plants include, but are not limited to, 3'nos, 3'35S, 3'his and 3'g7.

The "catalytic domain" of a glycosyltransferase is the domain of the glycosyltransferase conferring catalytic activity. The catalytic domain has been well-defined for several glycosyltransferases such as, for example, Rabbit GnTI (Sarkar et. al., 1998, Glycoconj. J. 15:193). Catalytic domains of other Golgi glycosyltransferases can be identified using methods well-known in the art such as, for example, protein secondary structure prediction, sequence alignments with known catalytic domains of Golgi glycosyltransferases, or determining catalytic activity of truncated proteins.

As used herein, the term "CTS domain" is the cytoplasmic tail, transmembrane domain, stem region of Golgi-resided proteins, including, but not limited to glycosyltransferases, that mediate sorting of these proteins into different functional subcompartmental areas of the Golgi. The CTS domain has been well-defined for several glycosyltransferases such as, for example, the *Arabidopsis thaliana* beta(1,2)-xylosyltransferase (Dirnberger et. al., 2002, Plant Mol. Biol. 50: 273), the rat alfa(2,6)-sialyltransferase (Munro, 1991, EMBO J. 10:3577), and the tobacco N-acetylglucosaminyltransferase I (Essl et. al., 1999, FEBS Lett. 453:169).

The CTS region of other Golgi-resided proteins can be identified using methods well-known in the art, such as, for example, hydropathy plot analyses and sequence alignments with known CTS regions and the catalytic domains of Golgi glycosyltransferases. Examples of CTS domains include, but are not limited to, AA 1 to 80 of the *Xenopus tropicalis* GalT (SEQ ID NO:8), AA 1 to 61 of rat sialyltransferase. A CTS domain can consist of a substantial part of a CTS domain, such as at least 50%, or at least 60%, or at least 70%, or at least 80%, or at least 90% of a CTS domain. An example of a substantial part of a CTS domain includes, but is not limited to, AA 1 to 52 of the rat sialyltransferase (SEQ ID NO:7).

A "stem region" is the lumenal part of the CTS domain. The stem region has been well-defined for, for example, the rabbit Rabbit GnTI (Sarkar et. al., 1998, Glycoconj. J. 15:193). Stem regions of other Golgi glycosyltransferases can be identified using methods well-known in the art such as, for example, hydropathy plot analyses, secondary structure prediction, and sequence alignments with known stem regions, CTS regions and catalytic domains of Golgi glycosyltransferases. Examples of stem regions include, but are not limited to, AA 48 to 80 of the *Xenopus tropicalis* GalT (SEQ ID NO:10) and AA 27 to of rat sialyltransferase. A stem region may contain additional amino acids. Said additional amino acids can be located at the N-terminal or C-terminal, or both N- and C-terminal of the stem region. A stem region may also consist of a substantial part of the stem region, such as at least 50%, or at least 60%, or at least 70%, or at least 80%, or at least 90% of a stem region. An example of a substantial part of a stem region includes, but is not limited to, AA 27 to 52 of the rat sialyltransferase (SEQ ID NO:9).

A "duplicated stem", or "duplicated stem region", or "duplication of the stem region" as used herein is the presence of two times the stem region of a Golgi-resided protein, including, but not limited to, a glycosyltransferase. Said duplicated stem can comprise a duplication of the stem region of a single Golgi-resided protein. Said duplicated stem can also comprise of one stem region of a first Golgi-resided protein and one stem region of a second Golgi-resided protein. The stem region in the duplicated stem may also consist of a substantial part of the stem region, such as at least 50%, or at least 60%, or at least 70%, or at least 80%, or at least 90% of a stem region. An example of a substantial part of a stem region includes, but is not limited to, AA 27 to 52 of the rat sialyltransferase (SEQ ID NO:9). The stem region in the duplicated stem may comprise additional amino acids. Said additional amino acids can be located at the N-terminal or C-terminal, or both N- and C-terminal of the stem region or of a substantial part of the stem region.

In another embodiment, the invention provides a method to increase levels of bi-antennary N-glycans comprising at least one terminal beta(1,4)-galactose residue and to decrease levels of hybrid-type beta(1,4)-galactosylated N-glycans on glycoproteins produced in a plant or plant cell comprising the steps of providing a plant cell with a chimeric gene comprising a plant-expressible promoter, a DNA region encoding a CTS domain operably linked to the stem region and the catalytic domain of a beta(1,4)-galactosyltransferase, and a DNA region involved in transcription termination and polyadenylation, and cultivating said plant cell and isolating beta(1,4)-galactosylated glycoproteins from said plant cell.

"Hybrid-type glycans" as herein described refers to N-glycan structures with both substituted and unsubstituted mannose residues. Examples of hybrid-type N-glycans are, but are not limited to, Man4A and Man5A.

Decreased levels of hybrid-type beta(1,4)-galactosylated N-glycans can be a decrease in the abundance of Man4A structures, or can be a decrease in the abundance of Man5A structures, or can be a decrease in the abundance of both Man4A and Man5A structures.

"Man4A structures" as used herein refers to a hybrid-type glycan structure having 4 Mannose residues and one terminal Galactose residue.

"Man5A structures" as used herein refers to a hybrid-type glycan structure having 5 Mannose residues and one terminal Galactose residue.

In a particular embodiment, the CTS domain is a CTS domain capable of targeting proteins to the trans-golgi compartment. In another particular embodiment, the CTS domain is of rat alfa(2,6)-sialyltransferase. Said CTS domain of rat alfa(2,6)-sialyltransferase may consist of AA 1 to 61 of rat alfa(2,6)-sialyltransferase, or a substantial part thereof, such as AA 1 to 52 of the rat alfa(2,6)-sialyltransferase (SEQ ID NO:7).

The "trans-golgi" compartment as used herein is the final region of the Golgi apparatus, distal from the endoplasmic reticulum.

In a particular embodiment, said beta(1,4)-galactosyltransferase is the *Xenopus tropicalis* beta(1,4)-galactosyltransferase. In another embodiment, said DNA region encodes the polypeptide comprising at least 90% similarity to SEQ ID NO:3 and, in another embodiment, said DNA region comprises at least 90% sequence identity to SEQ ID NO:2.

For the purpose of this invention, the "sequence identity" of two related nucleotide sequences, expressed as a percentage, refers to the number of positions in the two optimally aligned sequences which have identical residues (×100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman and Wunsch (1970) J Mol Biol. 48:443) The computer-assisted sequence alignment above, can be conveniently performed using standard software program such as GAP which is part of the Wisconsin Package Version 10.1 (Genetics Computer Group, Madision, Wis., USA) using the default scoring matrix with a gap creation penalty of 50 and a gap extension penalty of 3. It is clear that when RNA sequences have a certain degree of sequence identity with DNA sequences, thymine (T) in the DNA sequence is considered equal to uracil (U) in the RNA sequence.

Sequence similarity of protein sequences uses a substitution matrix with scores for all possible exchanges of one amino acid with another. The degree of similarity between protein sequences can, for example, be evaluated with the BLOSUM 62 substitution matrix (Henikoff and Henikoff, 1992, Proc. Natl. Acad. Sci. U.S.A. 89:10915).

It is another object to provide a method to increase levels of beta(1,4)-galactosylation or to decrease the levels of hybrid-type beta(1,4)-galactosylated N-glycans on protein-bound N-glycans produced in a plant or plant cell having reduced beta(1,2)-xylosyltransferase and reduced alfa(1,3)-fucosyltransferase activity.

"Reduced beta(1,2)-xylosyltransferase activity" and "reduced alfa(1,3)-fucosyltransferase activity" is a reduction in activity as compared to the activity in plants with wild-type levels of beta(1,2)-xylosyltransferase and alfa(1,3)-fucosyltransferase activity. Said reduction can be a reduction of at least 50%, or at least 60%, or at least 70%, or at least 80%, or at least 90%, or at least 95%, or can be complete elimination of activity of beta(1,2)-xylosyltransferase or alfa(1,3)-fucosyltransferase. The reduction of beta(1,2)-xylosyltransferase activity can be higher than that of alfa(1,3)-fucosyltransferase activity, or can be the same as that of alfa(1,3)-fucosyltransferase, or can be lower than that of alfa(1,3)-fucosyltransferase.

The level of beta(1,2)-xylosyltransferase and alfa(1,3)-fucosyltransferase activity can conveniently be reduced or eliminated by identifying plant cells having a null mutation in all of the genes encoding beta(1,2)-xylosyltransferase and in all of the genes encoding alfa(1,3)-fucosyltransferase.

The art provides for numerous methods to isolate and identify plant cells having a mutation in a particular gene.

Mutants having a deletion or other lesion in the alfa(1,3)-fucosyltransferase or beta(1,2)-xylosyltransferase encoding genes can conveniently be recognized using, e.g., a method named "Targeting induced local lesions in genomes (TILLING)". Plant Physiol. 2000 June; 123(2):439-42. Plant cells having a mutation in the desired gene may also be identified in other ways, e.g., through amplification and nucleotide sequence determination of the gene of interest. Null mutations may include, e.g., genes with insertions in the coding region or gene with premature stop codons or mutations which interfere with the correct splicing. Mutants may be induced by treatment with ionizing radiation or by treatment with chemical mutagens such as EMS.

Genes encoding alfa(1,3)-fucosyltransferase (FucT) in plants are well known and include the following database entries identifying experimentally demonstrated and putative FucT cDNA and gene sequences, parts thereof or homologous sequences: NM 112815 (*Arabidopsis thaliana*), NM103858 (*Arabidopsis thaliana*), AJ 618932 (*Physcomitrella patens*) At1g49710 (*Arabidopsis thaliana*) and At3g19280 (*Arabidopsis thaliana*). DQ789145 (*Lemna minor*), AY557602 (*Medicago truncatula*) Y18529 (*Vigna radiata*) AP004457 (*Oryza sativa*), AJ891040 encoding protein CAI70373 (*Populus alba×Populus tremula*) AY082445 encoding protein AAL99371 (*Medicago sativa*) AJ582182 encoding protein CAE46649 (*Triticum aestivum*) AJ582181 encoding protein CAE46648 (*Hordeum vulgare*) (all sequences herein incorporated by reference).

Genes encoding beta(1,2)-xylosyltransferase (XylT) in plants are well known and include the following database entries identifying experimentally demonstrated and putative XylT cDNA and gene sequences, parts thereof or homologous sequences: AJ627182, AJ627183 (*Nicotiana tabacum* cv. Xanthi), AM179855 (*Solanum tuberosum*), AM179856 (*Vitis vinifera*), AJ891042 (*Populus alba×Populus tremula*), AY302251 (*Medicago sativa*), AJ864704 (*Saccharum officinarum*), AM179857 (*Zea mays*), AM179853 (*Hordeum vulgare*), AM179854 (*Sorghum bicolor*), BD434535, AJ277603, AJ272121, AF272852, AX236965 (*Arabidopsis thaliana*), AJ621918 (*Oryza sativa*), AR359783, AR359782, AR123000, AR123001 (Soybean), AJ618933 (*Physcomitrella patens*) and At5g55500 (*Arabidopsis thaliana*) as well as the nucleotide sequences from *Nicotiana* species described in WO/2007/107296 (all sequences herein incorporated by reference).

Based on the available sequences, the skilled person can isolate genes encoding alfa(1,3)-fucosyltransferase or genes encoding beta(1,2)-xylosyltransferase from plants other than the plants mentioned above. Homologous nucleotide sequence may be identified and isolated by hybridization under stringent conditions using as probes identified nucleotide sequences.

Nucleotide sequences obtained in this way should be verified for encoding a polypeptide having an amino acid sequence which is at least 60%, 65%, 70%, 75%, 80%, 85%, 90% or 95% identical to a known alfa(1,3)-fucosyltransferase or beta(1,2)-xylosyltransferase from plants.

Other sequences encoding alfa(1,3)-fucosyltransferase or beta(1,2)-xylosyltransferase may also be obtained by DNA amplification using oligonucleotides specific for genes encoding alfa(1,3)-fucosyltransferase or beta(1,2)-xylosyltransferase as primers, such as but not limited to oligonucleotides comprising or consisting of about 20 to about 50 consecutive nucleotides from the known nucleotide sequences or their complement.

The level of beta(1,2)-xylosyltransferase and alfa(1,3)-fucosyltransferase activity can also conveniently be reduced or eliminated by transcriptional or post-transcriptional silencing of the expression of endogenous beta(1,2)-xylosyltransferase and alfa(1,3)-fucosyltransferase encoding genes. To this end a silencing RNA molecule is introduced in the plant cells targeting the endogenous beta(1,2)-xylosyltransferase and alfa(1,3)-fucosyltransferase encoding genes. As used herein, "silencing RNA" or "silencing RNA molecule" refers to any RNA molecule, which upon introduction into a plant cell, reduces the expression of a target gene. Such silencing RNA may, e.g., be so-called "antisense RNA", whereby the RNA molecule comprises a sequence of at least 20 consecutive nucleotides having 95% sequence identity to the complement of the sequence of the target nucleic acid, preferably the coding sequence of the target gene. However, antisense RNA may also be directed to regulatory sequences of target genes, including the promoter sequences and transcription termination and polyadenylation signals. Silencing RNA further includes so-called "sense RNA" whereby the RNA molecule comprises a sequence of at least 20 consecutive nucleotides having 95% sequence identity to the sequence of the target nucleic acid. Other silencing RNA may be "unpolyadenylated RNA" comprising at least 20 consecutive nucleotides having 95% sequence identity to the complement of the sequence of the target nucleic acid, such as described in WO01/12824 or U.S. Pat. No. 6,423,885 (both documents herein incorporated by reference). Yet another type of silencing RNA is an RNA molecule as described in WO03/076619 (herein incorporated by reference) comprising at least 20 consecutive nucleotides having 95% sequence identity to the sequence of the target nucleic acid or the complement thereof, and further comprising a largely-double stranded region as described in WO03/076619 (including largely double stranded regions comprising a nuclear localization signal from a viroid of the Potato spindle tuber viroid-type or comprising CUG trinucleotide repeats). Silencing RNA may also be double stranded RNA comprising a sense and antisense strand as herein defined, wherein the sense and antisense strand are capable of base-pairing with each other to form a double stranded RNA region (preferably the said at least 20 consecutive nucleotides of the sense and antisense RNA are complementary to each other). The sense and antisense region may also be present within one RNA molecule such that a hairpin RNA (hpRNA) can be formed when the sense and antisense region form a double stranded RNA region. hpRNA is well-known within the art (see, e.g., WO99/53050, herein incorporated by reference). The hpRNA may be classified as long hpRNA, having long, sense and antisense regions which can be largely complementary, but need not be entirely complementary (typically larger than about 200 bp, ranging between 200-1000 bp). hpRNA can also be rather small ranging in size from about 30 to about 42 bp, but not much longer than 94 by (see WO04/073390, herein incorporated by reference). Silencing RNA may also be artificial micro-RNA molecules as described, e.g., in WO2005/052170, WO2005/047505 or U.S. 2005/0144667, or ta-siRNAs as described in WO2006/074400 (all documents incorporated herein by reference).

In another object of the invention, a method is provided to increase levels of beta(1,4)-galactosylation or decrease the levels of hybrid-type beta(1,4)-galactosylated N-glycans on heterologous glycoproteins produced in a plant or plant cell expressing said heterologous glycoprotein.

In another object of the invention, a method is provided to increase levels of beta(1,4)-galactosylation or decrease the levels of hybrid-type beta(1,4)-galactosylated N-glycans on heterologous glycoproteins produced in a plant or plant cell expressing said heterologous glycoprotein, wherein said plant or plant cell has reduced beta(1,2)-xylosyltransferase and reduced alfa(1,3)-fucosyltransferase activity.

In yet another object of the invention, a method is provided to increase levels of beta(1,4)-galactosylation or decrease the levels of hybrid-type beta(1,4)-galactosylated N-glycans on heterologous glycoproteins produced in a plant or plant cell expressing said heterologous glycoprotein, further comprising the step of purification of said heterologous glycoprotein.

"Purification" as used herein is to isolate the heterologous protein from the mixture of total plant proteins. The level of purification can be to at least 50% purity, or to at least 60% purity, or to at least 70% purity, or to at least 80% purity, or to at least 85% purity, or to at least 90% purity, or to at least 95% purity, or to at least 98% purity, or to at least 99% purity.

Methods for protein purification are well-known in the art and may consist of, but are not limited to, differential precipitation, ultracentrifugation, chromatography, or affinity purification.

Heterologous glycoproteins, i.e., glycoproteins which are not normally expressed in such plant cells in nature, may include mammalian or human proteins, which can be used as therapeutics such as, e.g., monoclonal antibodies. Conveniently, the foreign glycoproteins may be expressed from chimeric genes comprising a plant-expressible promoter and the coding region of the glycoprotein of interest, whereby the chimeric gene is stably integrated in the genome of the plant cell. Methods to express foreign proteins in plant cells are well known in the art. Alternatively, the foreign glycoproteins may also be expressed in a transient manner, e.g., using the viral vectors and methods described in WO02/088369, WO2006/079546 and WO2006/012906 or using the viral vectors described in WO89/08145, WO93/03161 and WO96/40867 or WO96/12028.

By "heterologous protein" it is understood a protein (i.e., a polypeptide) that is not expressed by the plant or plant cells in nature. This is in contrast with a homologous protein which is a protein naturally expressed by a plant or plant cell. Heterologous and homologous polypeptides that undergo post-translational N-glycosylation are referred to herein as heterologous or homologous glycoproteins.

Examples of heterologous proteins of interest that can be advantageously produced by the methods of this invention include, without limitation, cytokines, cytokine receptors, growth factors (e.g., EGF, HER-2, FGF-alpha, FGF-beta, TGF-alpha, TGF-beta, PDGF, IGF-I, IGF-2, NGF), growth factor receptors. Other examples include growth hormones (e.g., human growth hormone, bovine growth hormone); insulin (e.g., insulin A chain and insulin B chain), pro-insulin, erythropoietin (EPO), colony stimulating factors (e.g., G-CSF, GM-CSF, M-CSF); interleukins; vascular endothelial growth factor (VEGF) and its receptor (VEGF-R), interferons, tumor necrosis factor and its receptors, thrombopoietin (TPO), thrombin, brain natriuretic peptide (BNP); clotting factors (e.g., Factor VIII, Factor IX, von Willebrands factor and the like), anti-clotting factors; tissue plasminogen activator (TPA), urokinase, follicle stimulating hormone (FSH), luteinizing hormone (LH), calcitonin, CD proteins (e. g., CD2, CD3, CD4, CD5, CD7, CD8, CDl Ia, CDl Ib, CD18, CD19, CD20, CD25, CD33, CD44, CD45, CD71, etc.), CTLA proteins (e.g., CTLA4); T-cell and B-cell receptor proteins, bone morphogenic proteins (BNPs, e.g., BMP-I, BMP-2, BMP-3, etc.), neurotrophic factors, e.g., bone derived neurotrophic factor (BDNF), neurotrophins, e.g., rennin, rheumatoid factor, RANTES, albumin, relaxin, macrophage inhibitory protein (e.g., MIP-I, MIP-2), viral proteins or antigens, surface membrane proteins, ion channel proteins, enzymes, regulatory proteins, immunomodulatory proteins, (e.g., HLA, MHC, the B7 family), homing receptors, transport proteins, superoxide dismutase (SOD), G-protein coupled receptor proteins (GPCRs), neuromodulatory proteins, Alzheimer's Disease associated proteins and peptides. Fusion proteins and polypeptides, chimeric proteins and polypeptides, as well as fragments or portions, or mutants, variants, or analogs of any of the aforementioned proteins and polypeptides are also included among the suitable proteins, polypeptides and peptides that can be produced by the methods of the present invention. The protein of interest can be a glycoprotein. One class of glycoproteins is viral glycoproteins, in particular subunits, that can be used to produce for example a vaccine. Some examples of viral proteins comprise proteins from rhinovirus, poliomyelitis virus, herpes virus, bovine herpes virus, influenza virus, newcastle disease virus, respiratory syncitio virus, measles virus, retrovirus, such as human immunodeficiency virus or a parvovirus or a papovavirus, rotavirus or a coronavirus, such as transmissable gastroenteritisvirus or a flavivirus, such as tick-borne encephalitis virus or yellow fever virus, a togavirus, such as rubella virus or eastern-, western-, or venezuelean equine encephalomyelitis virus, a hepatitis causing virus, such as hepatitis A or hepatitis B virus, a pestivirus, such as hog cholera virus or a rhabdovirus, such as rabies virus.

The heterologous glycoprotein can be an antibody or a fragment thereof. The term "antibody" refers to recombinant antibodies (for example of the classes IgD, IgG, IgA, IgM, IgE) and recombinant antibodies such as single-chain antibodies, chimeric and humanized antibodies and multi-specific antibodies. The term "antibody" also refers to fragments and derivatives of all of the foregoing, and may further comprises any modified or derivatised variants thereof that retain the ability to specifically bind an epitope. Antibody derivatives may comprise a protein or chemical moiety conjugated to an antibody. A monoclonal antibody is capable of selectively binding to a target antigen or epitope. Antibodies include, monoclonal antibodies (mAbs), humanized or chimeric antibodies, camelized antibodies, camelid antibodies (nanobodies®), single chain antibodies (scFvs), Fab fragments, F(ab')$_2$ fragments, disulfide-linked Fvs (sdFv) fragments, anti-idiotypic (anti-Id) antibodies, intra-bodies, synthetic antibodies, and epitope-binding fragments of any of the above. The term "antibody" also refers to fusion protein that includes a region equivalent to the Fc region of an immunoglobulin. Also envisaged is the production in the plant or plant cells of the invention of so called dual-specificity antibodies (Bostrom J et. al. (2009) *Science* 323, 1610-1614).

Antibodies within the scope of the present invention include those comprising the amino acid sequences of the following antibodies: anti-HER2 antibodies including antibodies comprising the heavy and light chain variable regions (see U.S. Pat. No. 5,725,856) or Trastuzumab such as HERCEPTIN™; anti-CD20 antibodies such as chimeric anti-CD20 as in U.S. Pat. No. 5,736,137, a chimeric or humanized variant of the 2H7 antibody as in U.S. Pat. No. 5,721,108; anti-VEGF antibodies including humanized and/or affinity matured anti-VEGF antibodies such as the humanized anti-VEGF antibody huA4.6.1 AVASTIN™ (WO 96/30046 and WO 98/45331); anti-EGFR (chimerized or humanized antibody as in WO 96/40210); anti-CD3 antibodies such as OKT3 (U.S. Pat. No. 4,515,893); anti-CD25 or anti-tac antibodies such as CHI-621 (SIMULECT) and (ZENAPAX) (U.S. Pat. No. 5,693,762). The present invention provides a method for the production of an antibody which comprises culturing a transformed plant cell or growing a transformed plant of the present invention. The produced antibody may be purified and formulated in accordance with standard procedures.

The nucleotide sequences of the glycosyltransferases and/or the heterologous genes may be codon optimized to increase the level of expression within the plant. By codon optimization it is meant the selection of appropriate DNA nucleotides for the synthesis of oligonucleotide building blocks, and their subsequent enzymatic assembly, of a structural gene or fragment thereof in order to approach codon usage in plants.

Another embodiment of the invention provides a glycoprotein obtained by the methods according to the invention. Yet another embodiment of the invention provides a beta(1,4)-galactosylated glycoprotein obtained by the methods according to the invention.

In another embodiment, a plant or plant cell is provided comprising a chimeric gene comprising a plant-expressible promoter, a DNA region encoding a CTS domain operably linked to the stem region and the catalytic domain of the *Xenopus tropicalis* beta(1,4)-galactosyltransferase, and a DNA region involved in transcription termination and polyadenylation. In yet another embodiment, said CTS domain is the CTS domain of rat alfa(2,6)-sialyltransferase. In yet another embodiment, said plant or plant cell has reduced beta(1,2)-xylosyltransferase activity and reduced alfa(1,3)-fucosyltransferase activity. In yet another embodiment, said plant or plant cell comprises a heterologous glycoprotein which is expressed in said plant or plant cell from a chimeric gene comprising a plant expressible promoter and a DNA region encoding said heterologous glycoprotein.

In another embodiment, a chimeric gene is provided comprising a plant-expressible promoter, a DNA region encoding a CTS domain operably linked to the stem region and the catalytic domain of the *Xenopus tropicalis* beta(1,4)-galactosyltransferase, and a DNA region involved in transcription termination and polyadenylation.

In yet a further aspect according to the invention, the beta (1,4)-galactosyltransferase comprising a duplicated stem region is used to obtain glycoproteins having bi-antennary N-glycans comprising at least one terminal beta(1,4)-galactose residue in plants or plant cells for the production of heterologous proteins.

In certain embodiments methods for obtaining a desired glycoprotein or functional fragment thereof comprise cultivating a plant described herein until said plant has reached a harvestable stage, harvesting and fractionating the plant to obtain fractionated plant material and at least partly isolating said glycoprotein from said fractionated plant material.

In certain embodiments methods for obtaining a desired glycoprotein or functional fragment thereof comprise growing recombinant plant cells in cell culture in a fermentor until said cell culture has reached a harvestable stage or the desired glycoprotein can be collected from the medium. The glycoproteins described herein, such as, e.g., antibodies, vaccines, cytokines and hormones, may be purified by standard techniques well known to those of skill in the art. Such recombinantly produced proteins may be directly expressed or expressed as a fusion protein. The recombinant protein is purified by a combination of cell lysis (e.g., sonication, French press) and affinity chromatography or other affinity-based method. For fusion products, subsequent digestion of the fusion protein with an appropriate proteolytic enzyme releases the desired recombinant protein.

The proteins described herein, recombinant or synthetic, may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

The methods and means described herein are believed to be suitable for all plant cells and plants, gymnosperms and angiosperms, both dicotyledonous and monocotyledonous plant cells and plants including but not limited to *Arabidopsis,* alfalfa, barley, bean, corn or maize, cotton, flax, oat, pea, rape, rice, rye, safflower, sorghum, soybean, sunflower, tobacco and other *Nicotiana* species, including *Nicotiana benthamiana,* wheat, asparagus, beet, broccoli, cabbage, carrot, cauliflower, celery, cucumber, eggplant, lettuce, onion, oilseed rape, pepper, potato, pumpkin, radish, spinach, squash, tomato, zucchini, almond, apple, apricot, banana, blackberry, blueberry, cacao, cherry, coconut, cranberry, date, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut, watermelon, *Brassica* vegetables, sugarcane, vegetables (including chicory) and sugarbeet.

Methods for the introduction of chimeric genes into plants are well known in the art and include *Agrobacterium*-mediated transformation, particle gun delivery, microinjection, electroporation of intact cells, polyethyleneglycol-mediated protoplast transformation, electroporation of protoplasts, liposome-mediated transformation, silicon-whiskers mediated transformation etc. The transformed cells obtained in this way may then be regenerated into mature fertile plants.

A DNA sequence encoding a heterologous protein or polypeptide can encode translation codons that reflect the preferred codon usage of a plant cell or plant. For example, if the host cell or organism species is *Nicotiana benthamiana*, a codon usage table known in the art can be used to select codons or their complements in designing an artificial DNA sequence or modifying a naturally occurring DNA sequence. It is expected that use of preferred codons in a coding sequence will lead to higher efficiency of translation of a transgene (i.e., in the present case a heterologous protein, in particular a heterologous glycoprotein) in a transgenic plant cell or plant.

Gametes, seeds, embryos, progeny, hybrids of plants, or plant tissues including stems, leaves, stamen, ovaria, roots, meristems, flowers, seeds, fruits, fibers comprising the chimeric genes of the present invention, which are produced by traditional breeding methods are also included within the scope of the present invention.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region which is functionally or structurally defined, may comprise additional DNA regions etc.

Unless stated otherwise in the Examples, all recombinant techniques are carried out according to standard protocols as described in "Sambrook J and Russell D W (eds.) (2001) *Molecular Cloning: A Laboratory Manual*, 3rd Edition, Cold Spring Harbor Laboratory Press, New York" and in "Ausubel F A, Brent R, Kingston R E, Moore D D, Seidman J G, Smith J A and Struhl K (eds.) (2006) *Current Protocols in Molecular Biology*. John Wiley & Sons, New York". Standard materials and references are described in "Croy R D D (ed.) (1993) *Plant Molecular Biology LabFax*, BIOS Scientific Publishers Ltd., Oxford and Blackwell Scientific Publications, Oxford" and in "Brown T A, (1998) *Molecular Biology LabFax*, 2nd Edition, Academic Press, San Diego". Standard materials and methods for polymerase chain reactions (PCR) can be found in "McPherson M J and Møller S G (2000) PCR (The Basics), BIOS Scientific Publishers Ltd., Oxford" and in "PCR Applications Manual, 3rd Edition (2006), Roche Diagnostics GmbH, Mannheim or www.roche-applied-science.com."

Throughout the description and Examples, reference is made to the following sequences:
SEQ ID NO:1: Expression cassette for Rn ST(CTS)-XtGalT (CAT)
SEQ ID NO:2: DNA encoding Rn ST(CTS)-XtGalT(CAT)
SEQ ID NO:3: Rn ST(CTS)-XtGalT(CAT) protein
SEQ ID NO:4: Expression cassette for Rn ST(CTS)-XtGalT (SCAT)
SEQ ID NO:5: DNA encoding Rn ST(CTS)-XtGalT(SCAT)
SEQ ID NO:6: Rn ST(CTS)-XtGalT(SCAT) protein
SEQ ID NO:7: CTS rat alfa(2,6)-sialyltransferase
SEQ ID NO:8: CTS *Xenopus tropicalis* beta(1,4)-Galactosyltransferase
SEQ ID NO:9: Stem region rat alfa(2,6)-sialyltransferase
SEQ ID NO:10: Stem region *Xenopus tropicalis* beta(1,4)-Galactosyltransferase
SEQ ID NO:11: Catalytic domain *Xenopus tropicalis* beta(1,4)-Galactosyltransferase

EXAMPLES

1. Expression Constructs for Transient Infiltrations of Chimeric Rn ST(CTS)-XtGalT(CAT) and Rn ST(CTS)-XtGalT (SCAT) in *Nicotiana benthamiana*

Hybrid expression constructs were generated based on the cytoplasmic tail, transmembrane domain, and stem region (CTS domain) of sialyltransferase from *Rattus norvegicus* (Wee et. al. (1998) Plant Cell 10: 1759) in combination with the catalytic domain (XtGalT(CAT)) or with the stem region and the catalytic domain (XtGalT(SCAT)) of beta(1,4)-galactosyltransferase from *Xenopus tropicalis*, resulting in Rn ST(CTS)-XtGalT(CAT) ("single stem") and Rn ST(CTS)-XtGalT(SCAT) ("double stem"), respectively.

For construction of a vector expressing Rn ST(CTS)-XtGalT(CAT), a synthetic fragment coding Cab22L-RnST (CTS)-XtGalT(5'CAT) (AA81-AA136), codon optimized for *Nicotiana benthamiana* was cloned into the SmaI sites of the vector pEN08H (Entelechon), resulting in pSH142.

A synthetic fragment containing the full-length XtGalT, was cloned into a T-DNA vector containing glyphosate tolerance, under control of a CAMV 35S promoter (pTSH081). A SalI-MluI fragment from pSH142, containing Cab22L-RnST (CTS)-XtGalT(5'SCAT) (AA48-AA136) was cloned into XhoI-MluI digested pTSH081, resulting in pTSH162. pTSH162 thus encodes Rn ST(CTS)-XtGalT(CAT) ("single stem") The sequence encoding Rn ST(CTS)-XtGalT(CAT) as present in pTSH162 is shown in SEQ ID NO:1.

For construction of a vector expressing Rn ST(CTS)-XtGalT(SCAT), a synthetic fragment containing Cab22L-RnST (CTS)-XtGalT(5'SCAT) (AA48-AA136), codon optimized for *Nicotiana benthamiana* was cloned into the SmaI sites of the vector pEN08H (Entelechon), resulting in pSH163.

A SalI-MluI fragment from pSH163, containing Cab22L-RnST(CTS)-XtGalT(5'SCAT) (AA48-AA136) was cloned into XhoI-MluI digested pTSH081, resulting in pTSH164. pTSH164 thus encodes Rn ST(CTS)-XtGalT(SCAT) ("double stem"). The sequence encoding Rn ST(CTS)-XtGalT(SCAT) as present in pTSH164 is shown in SEQ ID NO:4.

The resulting recombinant vectors were transformed into the *Agrobacterium tumefaciens* strain C58C1Rif(pGV4000) for stable transformation in *Nicotiana benthamiana*.

2. Analysis of Galactosylation of N-glycans on Endogenous Proteins of *N. benthamiana* Plants Expressing Rn ST(CTS)-XtGalT(CAT) and Rn ST(CTS)-XtGalT(SCAT)

*Nicotiana benthamiana* plants with a reduced expression of xylosyltransferase and fucosyltransferase (further herein designated as XylT/FucT RNAi plants as described in WO2008141806) were used to stably express hybrid Rn ST(CTS)-XtGalT(CAT) and Rn ST(CTS)-XtGalT(SCAT). To this end, the constructs pTSH162 and pTSH164, respectively, were used to transform the plants. All plants were transformed via leaf disk transformation (Regner et. al. (1992) Plant Cell Rep. 11: 30). Glyphosate resistant plants were screened by Real-time PCR to confirm genomic insertion of the hybrid GalT constructs and identify single copy plants. Real-time PCR was performed on genomic DNA with the TaqMan® Universal PCR Master mix (Applied Biosystems, Foster City, Calif.) using the 7500 Fast Real-Time PCR System (Applied Biosystems). The copy numbers of all samples were calculated by using the $2^{-\Delta\Delta Ct}$ method (Livak et. al. 2001).

Figure 2:
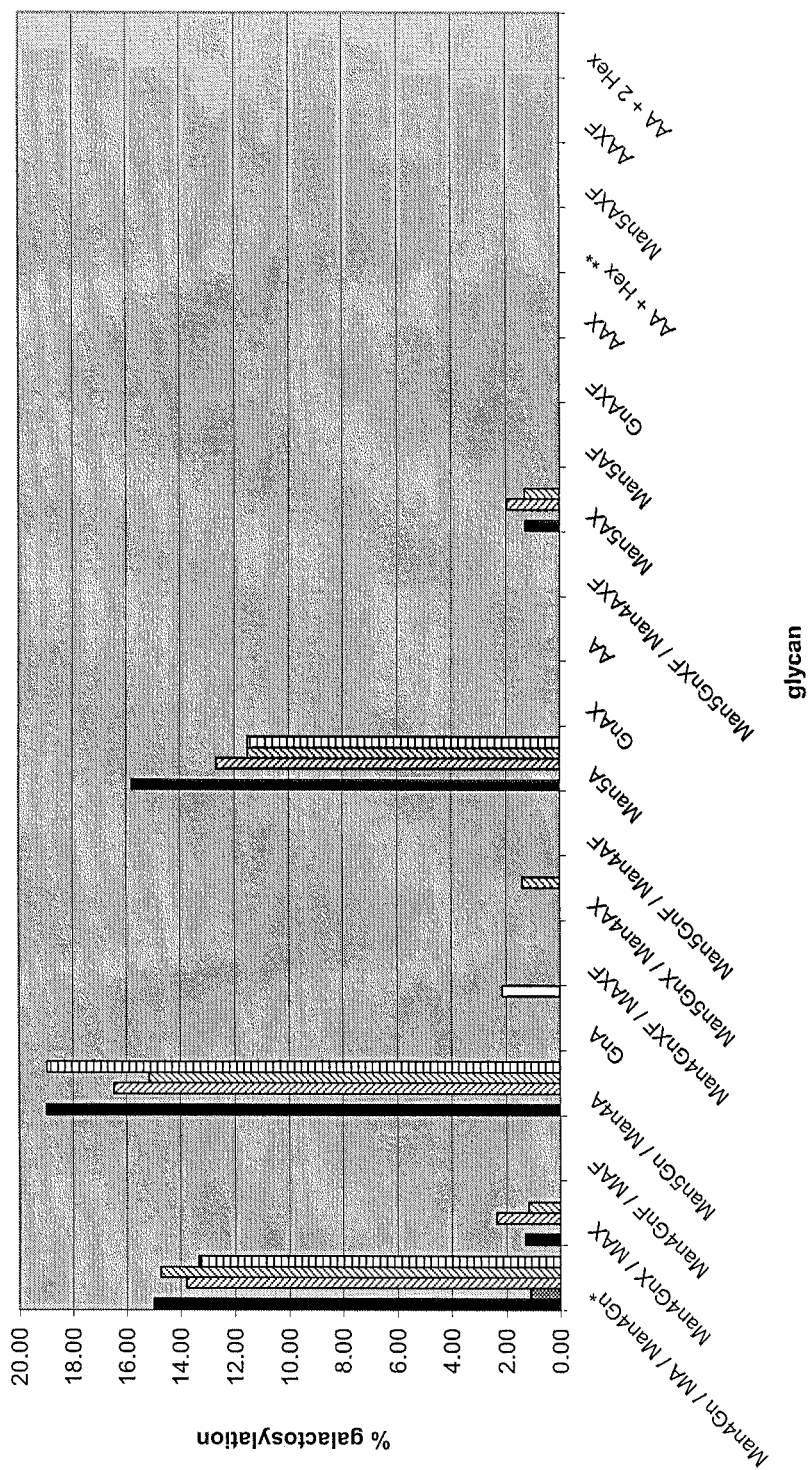
FIG. 2: MALDI-TOF MS analysis of endogenous glycosylated proteins in a xylosyltransferase negative and fucosyltransferase negative (XylT/FucT RNAi) background of *Nicotiana benthamiana* expressing ST(CTS)-XtGalT(CAT). 6401 (black bars), 6103 (hatched bars), 6404 (diagonally striped bars top left to bottom right), 6406 (diagonally striped bars bottom left to top right) and 6410 (horizontally striped bars) are different transgenic lines expressing ST(CTS)-XtGalT(CAT); white bars represent the XylT/FucT RNAi line not expressing ST(CTS)-XtGalT(CAT).
Figure 3A:
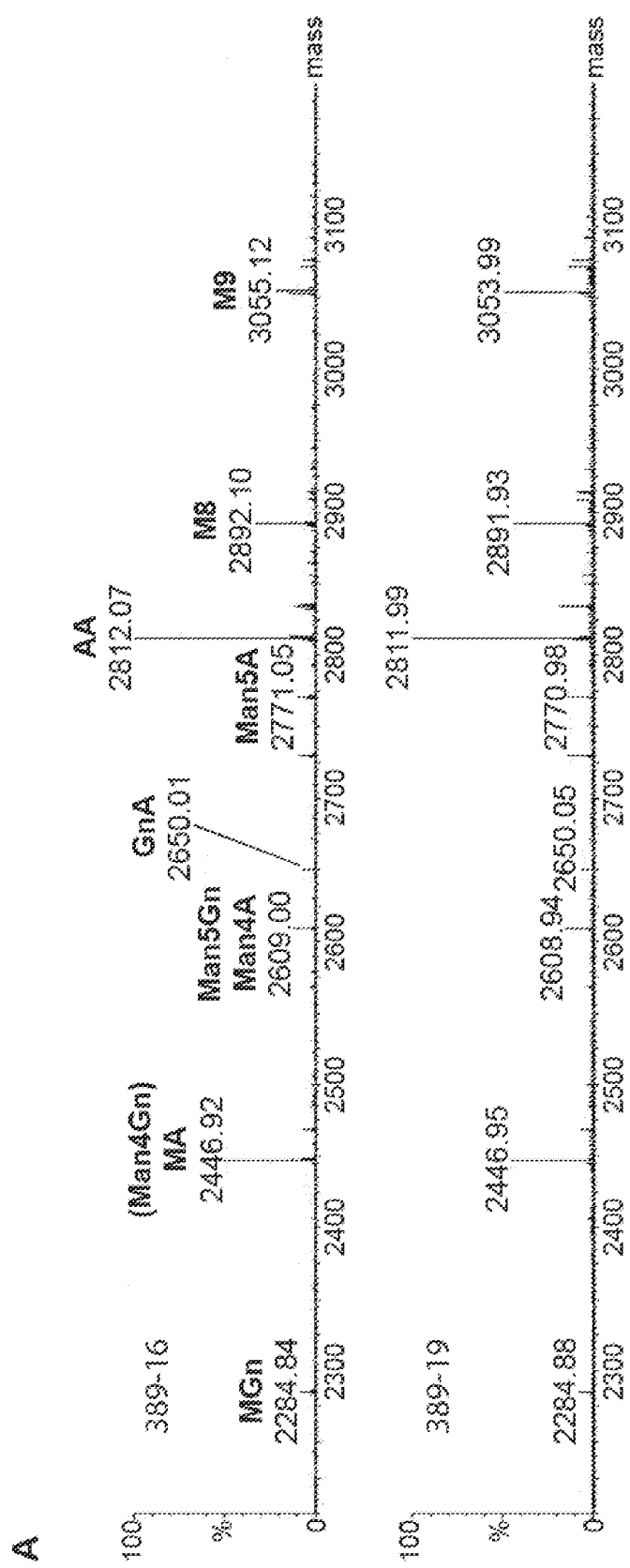
FIG. 3: LC-ESI-MS analysis of N-glycans on IgG1 expressed in:
a XylT-FucT-RNAi line of *Nicotiana benthamiana* expressing ST(CTS)-XtGalT(SCAT) line 389 (FIG. 3A) and line 390 (FIG. 3B)
a XylT-FucT-RNAi line of *Nicotiana benthamiana* expressing ST(CTS)-XtGalT(CAT) line 395 (FIG. 3C) and line 397 (FIG. 3D).
Figure 3B:
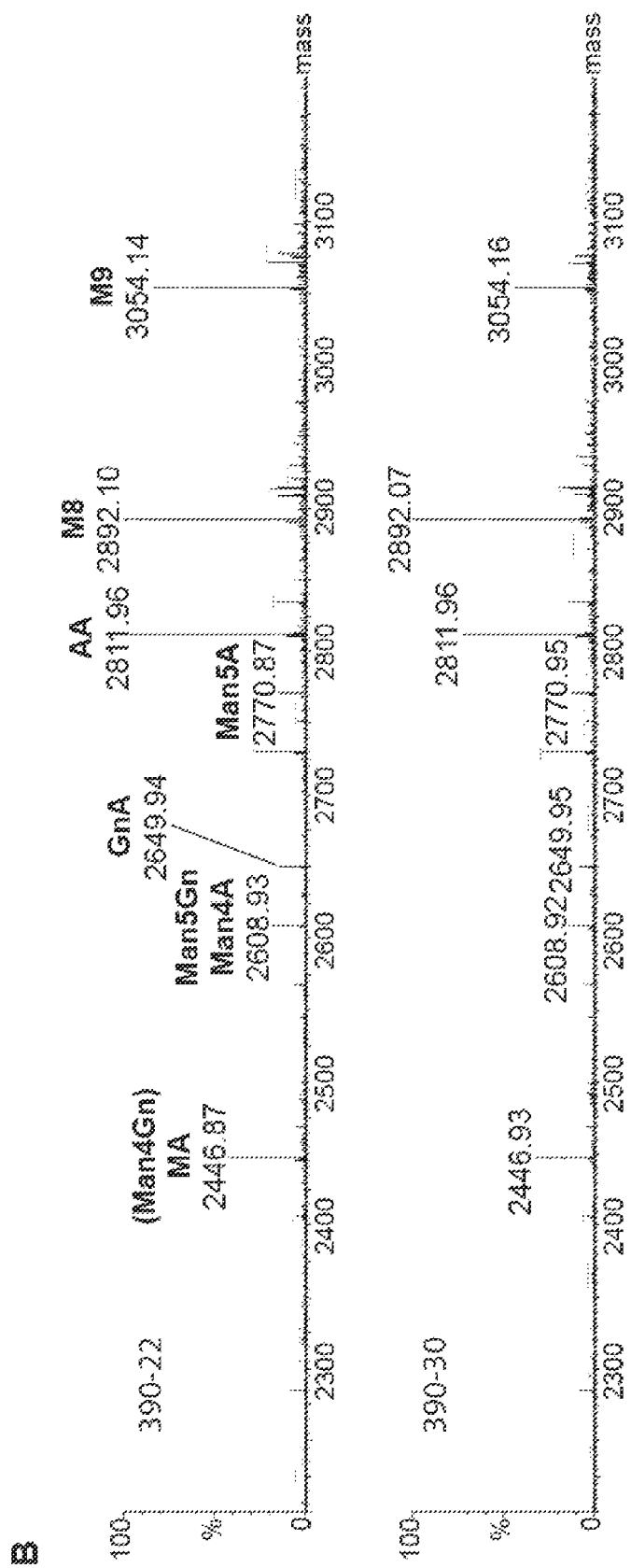
Figure 3C:
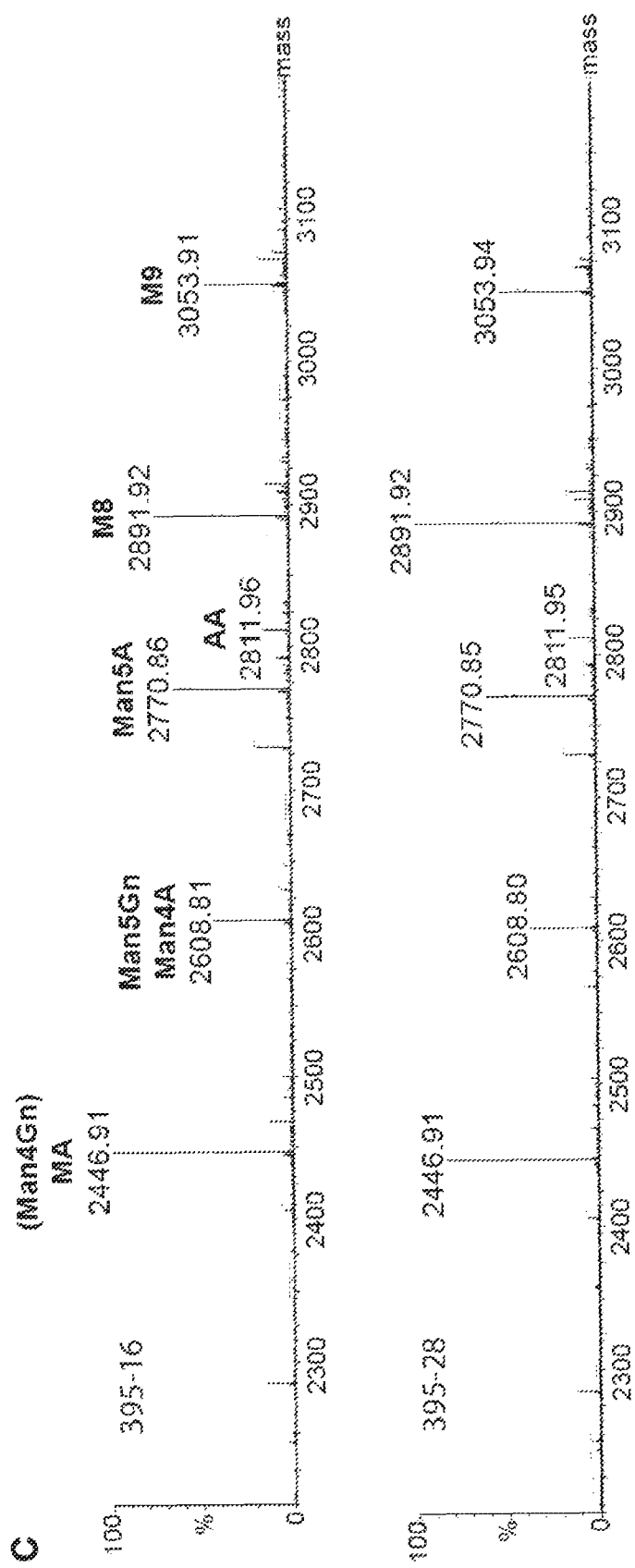
Figure 3D:
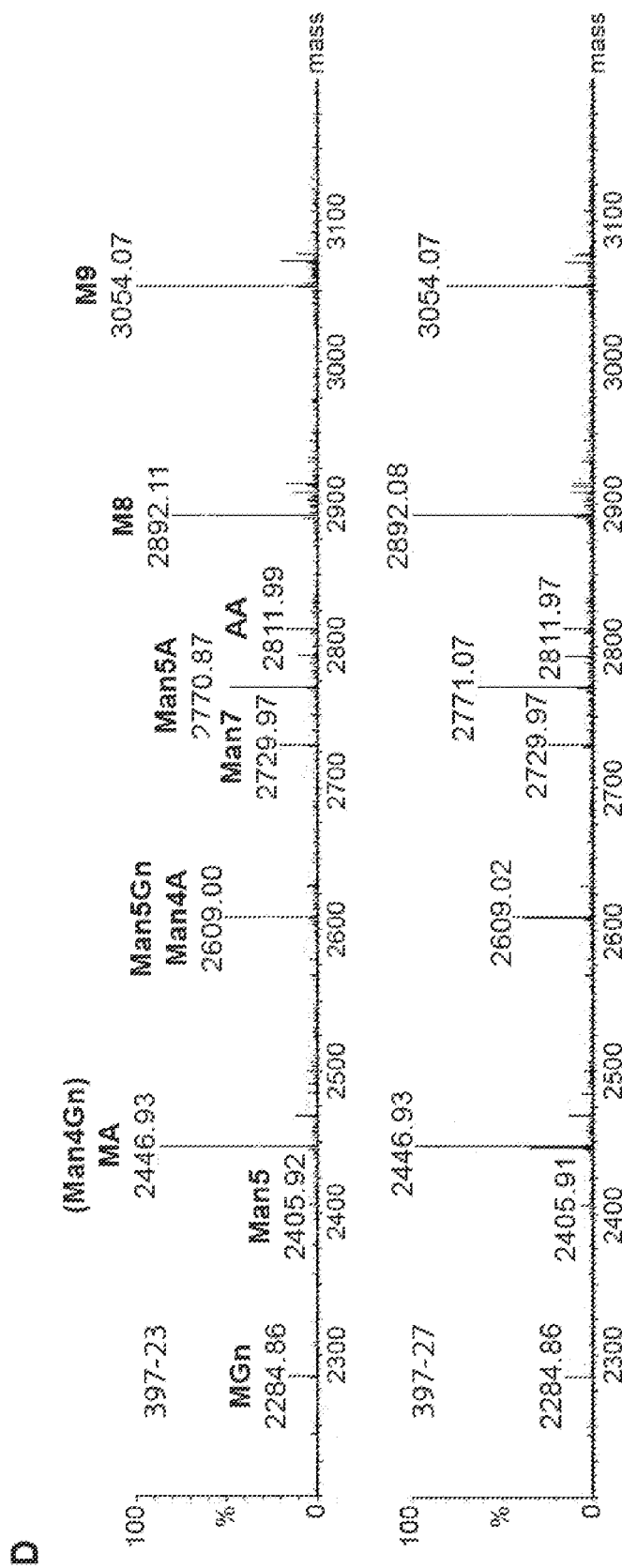

Leaves of five single copy events resulting from transformation of N. benthamina with either pTSH162 (Rn ST(CTS)-XtGalT(CAT)) or pTSH164 (Rn ST(CTS)-XtGalT(SCAT)) were harvested and the endogenous proteins were analyzed for their N-glycan content using matrix-assisted laser desorption ionization-time of flight mass spectrometry (MALDI-TOF MS) as outlined in Kolarich et. al. (2000) Anal. Biochem. 285, 64. Results of this analysis are presented in FIGS. 1 and 2 and Tables 1 and 2.

TABLE 1

MALDI-TOF MS analysis of the N-glycans on endogenous proteins of XylT/FucT RNAi N. benthamiana plants transformed with pTSH164 (Rn ST(CTS)-XtGalT(SCAT)). For the different lines the relative abundance of the glycans containing 1 or 2 galactoses and of the hybrid glycans containing 1 galactose are given.

| GZNB0063-00201 | |
| --- | --- |
| 2gal | 0% |
| 1gal | 0% |
| 1gal hybrid | 22% |
| total | 22% |
| GZNB0063-00301 | |
| 2gal | 2% |
| 1gal | 0% |
| 1gal hybrid | 24% |
| total | 26% |
| GZNB0063-00501 | |
| 2gal | 2% |
| 1gal | 0% |
| 1gal hybrid | 22% |
| total | 24% |
| GZNB0063-00901 | |
| 2gal | 0% |
| 1gal | 0% |
| 1gal hybrid | 9% |
| total | 9% |
| GZNB0063-01501 | |
| 2gal | 0% |
| 1gal | 0% |
| 1gal hybrid | 18% |
| total | 18% |

TABLE 2

MALDI-TOF MS analysis of the N-glycans on endogenous proteins of XylT/FucT RNAi N. benthamiana plants stably transformed with pTSH162 (Rn ST(CTS)-XtGalT(CAT)). For the different lines the relative abundance of the glycans containing 1 or 2 galactoses and of the hybrid glycans containing 1 galactose are given.

| GZNB0064-00101 | |
| --- | --- |
| 2gal | 0% |
| 1gal | 0% |
| 1gal hybrid | 29% |
| total | 29% |
| GZNB0064-00301 | |
| 2gal | 0% |
| 1gal | 1% |
| 1gal hybrid | 0% |
| total | 0% |

TABLE 2-continued

MALDI-TOF MS analysis of the N-glycans on endogenous proteins of XylT/FucT RNAi N. benthamiana plants stably transformed with pTSH162 (Rn ST(CTS)-XtGalT(CAT)). For the different lines the relative abundance of the glycans containing 1 or 2 galactoses and of the hybrid glycans containing 1 galactose are given.

| GZNB0064-00401 | |
| --- | --- |
| 2gal | 0% |
| 1gal | 0% |
| 1gal hybrid | 28% |
| total | 28% |
| GZNB0064-00601 | |
| 2gal | 0% |
| 1gal | 0% |
| 1gal hybrid | 25% |
| total | 25% |
| GZNB0064-01001 | |
| 2gal | 0% |
| 1gal | 0% |
| 1gal hybrid | 31% |
| total | 31% |

From the MALDI-TOF analysis it is observed that the percentage galactosyation of total protein varies between the different lines, and that there is no clear difference between the lines expressing Rn ST(CTS)-XtGalT(CAT) and Rn ST(CTS)-XtGalT(SCAT).

3. Galactosylation of N-glycans on Transiently Expressed IgG1 in Plants Comprising Rn ST(CTS)-XtGalT(CAT) or Rn ST(CTS)-XtGalT(SCAT)

In a next step we investigated the presence or absence of galactosylated N-glycans of a heterologous glycoprotein produced N. benthamiana expressing Rn ST(CTS)-XtGalT(CAT) or Rn ST(CTS)-XtGalT(SCAT) and comprising XylT/FucT RNAi. Thereto, we analyzed the N-glycans present on the heavy chain of an IgG1 expressed using magnICON® (Marillonnet et. al. (2005) Nature Biotechnology 23, 718-723). Ten days after infiltration, total protein was extracted from these plants and IgG1 was purified using protein G. The heavy chain of the purified antibody was isolated by cutting the corresponding band from a reducing SDS-PAGE. The heavy chain protein in this band was used for glycan analysis by LC-MS as described by Kolarich et. al. (Kolarich, D., Weber, A., Turecek, P. L., Schwarz, H. P., and Altmann, F. (2006) Comprehensive glyco-proteomic analysis of human alpha1-antitrypsin and its charge isoforms. Proteomics. 6:3369-3380).

The Mass spectrometry data of tryptic peptides were analysed against the in silico generated tryptic digestion of the IgG1 amino acid sequence, employing the program "PeptideMass". Based on the tryptic peptide data set, the tryptic glycopeptide data-sets were generated by the addition of the respective glycan masses to the tryptic peptide masses of the glycopeptides.

Figure 4:
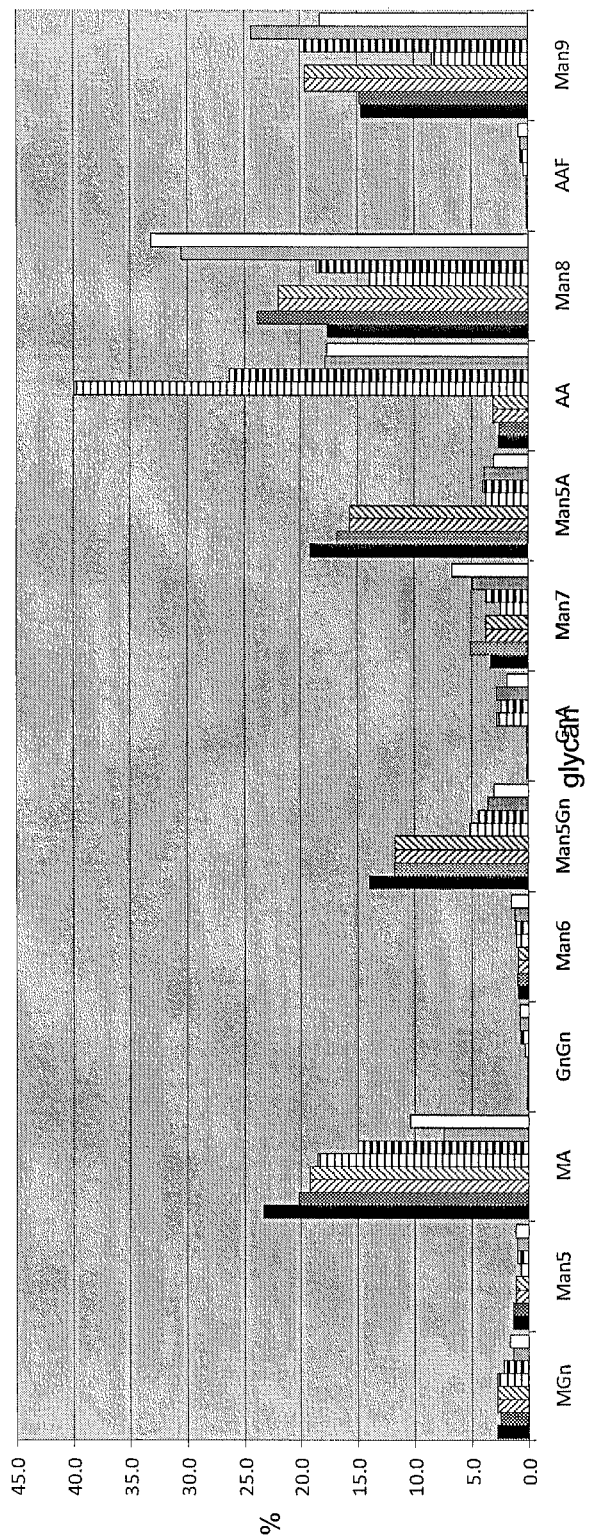
FIG. 4: Quantification of galactosylation of IgG expressed in a XylT-FucT-RNAi line of *Nicotiana benthamiana* expressing ST(CTS)-XtGalT(CAT) line 395-16 (black bars), 395-28 (hatched bars), 397-23 (diagonally striped bars top left to bottom right), 397-27 (diagonally striped bars bottom left to top right) or expressing ST(CTS)-XtGalT(SCAT) line 389-16 (horizontally striped bars, thin lines), 389-19 (horizontally striped bars, thick lines), 390-22 (grey bars) and 390-30 (white bars).

The results of the mass spectometric analyses are shown in FIGS. 3 and 4. These figures show that for the plants containing Rn ST(CTS)-XtGalT(SCAT), the levels of the galactosylated structure GnA and the fully galactosylated AA structure were higher on the expressed IgG1 than in plants containing Rn ST(CTS)-XtGalT(CAT). In addition, the levels of the hybrid Man4A and Man5A structures (see FIG. 3) are reduced on IgG1 expressed in the plants containing Rn ST(CTS)-XtGalT(SCAT) versus the IgG1 expressed in plants containing Rn ST(CTS)-XtGalT(CAT). Thus, the additional stem region of XtGalT in the Rn(CTS)-Xt GalT(SCAT) construct causes higher galactosylation levels and lower hybrid glycan levels. Moreover, these data show that, using Rn(CTS)-Xt GalT(SCAT), a total galactosylation level (AA and MA) of 60% can be reached.

The invention claimed is:

1. A method to increase levels of bi-antennary N-glycans comprising at least one terminal beta(1,4)-galactose residue on glycoproteins produced in a plant or plant cell, comprising the steps of:

a. providing a plant cell with a chimeric gene comprising the following operably linked nucleic acid molecules:
i. a plant-expressible promoter,
ii. a DNA region encoding a cytoplasmic tail, transmembrane and stem region (CTS domain) of an alpha (2,6)-sialytansferase operably linked to a stem region and a catalytic domain of a beta(1,4)-galactosyltransferase, wherein said stem region in the CTS is a first stem region and the stem region of the galactosyltansferase is a second stem region, and
   iii. a DNA region involved in transcription termination and polyadenylation; and
  b. cultivating said plant cell and isolating beta(1,4)-galactosylated glycoproteins from said plant cell.

2. A method to increase levels of bi-antennary N-glycans comprising at least one terminal beta(1,4)-galactose residue on heterologous glycoproteins produced in a plant or plant cell, comprising the steps of:
  a. providing a plant cell with a chimeric gene comprising the following operably linked nucleic acid molecules:
   i. a plant-expressible promoter,
   ii. a DNA region encoding a cytoplasmic tail, transmembrane and stem region (CTS domain) of an alpha(2,6)-sialyltransferase operably linked to a stem region and a catalytic domain of a beta(1,4)-galactosyltransferase, wherein said stem region in the CTS is a first stem region and the stem region of the galactosyltransferase is a second stem region, and
   iii. a DNA region involved in transcription termination and polyadenylation;
  b. expressing a heterologous protein in said plant or plant cell; and
  c. cultivating said plant cell and isolating the beta(1,4)-galactosylated heterologous glycoproteins from said plant cell.

3. A method to increase levels of bi-antennary N-glycans comprising at least one terminal beta(1,4)-galactose residue on heterologous glycoproteins produced in a plant or plant cell, comprising the steps of:
  a. providing a plant cell with a first chimeric gene comprising the following operably linked nucleic acid molecules:
   i. a plant-expressible promoter,
   ii. a DNA region encoding a cytoplasmic tail, transmembrane and stem region (CTS domain) of an alpha(2,6)-sialyltansferase operably linked to a stem region and a catalytic domain of a beta(1,4)-galactosyltransferase, wherein said stem region in the CTS is a first stem region and the stem region of the galactosyltransferase is a second stem region, and
   iii. a DNA region involved in transcription termination and polyadenylation;
  b. providing a plant cell with a second chimeric gene comprising the following operably linked nucleic acid molecules:
   i. a plant-expressible promoter,
   ii. a DNA region encoding said heterologous glycoprotein, and
   iii. a DNA region involved in transcription termination and polyadenylation; and
  c. cultivating said plant cell and isolating the beta(1,4)-galactosylated heterologous glycoproteins from said plant cell.

4. The method according to claim 2, further comprising the step of purification of said heterologous glycoprotein.

5. The method according to claim 1, further characterized in that the levels of hybrid-type beta(1,4)-galactosylated N-glycans on said glycoproteins are reduced compared to an isogenic plant or plant cell comprising a galactosyltransferase with one stem region only.

6. The method according to claim 1, in which said CTS domain is a CTS domain capable of targeting proteins to the trans-golgi compartment.

7. The method according to claim 6, in which said CTS domain is the CTS domain of rat alpha(2,6)-sialyltransferase.

8. The method according to claim 1, in which said beta(1,4)-galactosyltransferase is the *Xenopus tropicalis* beta(1,4)-galactosyltransferase.

9. The method according to claim 1, in which said DNA region encodes the polypeptide comprising at least 90% similarity to SEQ ID NO:6.

10. The method according to claim 1, in which said DNA region comprises at least 90% sequence identity to SEQ ID NO:5.

11. The method according to claim 1 wherein the plant cells have reduced beta(1,2)-xylosyltransferase activity and reduced alpha(1,3)-fucosyltransferase activity.

12. A beta(1,4)-galactosylated glycoprotein obtained by the method of claim 1.

13. A plant or plant cell comprising a chimeric gene comprising the following operably linked nucleic acid molecules:
  a. a plant-expressible promoter,
  b. a DNA region encoding a cytoplasmic tail, transmembrane and stem regions (CTS domain) of an alpha(2,6)-sialyltransferase operably linked to a stem region and a catalytic domain of a *Xenopus tropicalis* beta(1,4)-galactosyltransferase, wherein said stem region in the CTS is a first stem region and the stem region of the galactosyltansferase is a second stem region, and
  c. a DNA region involved in transcription termination and polyadenylation.

14. The plant or plant cell according to claim 13 wherein said plant or plant cell has reduced beta(1,2)-xylosyltransferase activity and reduced alpha(1,3)-fucosyltransferase activity.

15. The plant or plant cell according to claim 13 comprising a heterologous glycoprotein which is expressed in said plant or plant cell from a chimeric gene comprising a plant expressible promoter and a DNA region encoding said heterologous glycoprotein.

16. A chimeric gene comprising the following operably linked nucleic acid molecules:
  a. a plant-expressible promoter,
  b. a DNA region encoding a cytoplasmic tail, transmembrane and stem region (CTS domain) of an alpha(2,6)-sialyltansferase operably linked to a stem region and a catalytic domain of a *Xenopus tropicalis* beta(1,4)-galactosyltransferase, wherein said stem region in the CTS is a first stem region and the stem region of the galactosyltransferase is a second stem region, and
  c. a DNA region involved in transcription termination and polyadenylation.

\* \* \* \* \*

```
                            SEQUENCE LISTING

<160> NUMBER OF SEQ ID NOS: 11

<210> SEQ ID NO 1
<211> LENGTH: 1853
<212> TYPE: DNA
<213> ORGANISM: Artificial
<220> FEATURE:
<223> OTHER INFORMATION: Expression cassette for RN ST(CTS_XtGalT(CAT)
<220> FEATURE:
<221> NAME/KEY: promoter
<222> LOCATION: (1)..(528)
<223> OTHER INFORMATION: P35S2: Promoter region from CaMV35S gene
<220> FEATURE:
<221> NAME/KEY: 5'UTR
<222> LOCATION: (535)..(595)
<223> OTHER INFORMATION: 5'cab22L: untranslated leader sequence of
      cab22L gene from petunia
<220> FEATURE:
<221> NAME/KEY: misc_feature
<222> LOCATION: (602)..(757)
<223> OTHER INFORMATION: CTS of rat alfa(2,6)-sialyltransferase
<220> FEATURE:
<221> NAME/KEY: misc_feature
<222> LOCATION: (758)..(1606)
<223> OTHER INFORMATION: catalytic domain of Xenopus beta(1,4)-
      galactosyltransferase
<220> FEATURE:
<221> NAME/KEY: terminator
<222> LOCATION: (1630)..(1853)
<223> OTHER INFORMATION: 3'35S: 3' untranslated region from the CaMV35S
      gene

<400> SEQUENCE: 1
catggagtca aaaattcaga tcgaggatct aacagaactc gccgtgaaga ctggcgaaca      60
gttcatacag agtcttttac gactcaatga caagaagaaa atcttcgtca acatggtgga     120
gcacgacact ctcgtctact ccaagaatat caaagataca gtctcagaag accaaagggc     180
tattgagact tttcaacaaa gggtaatatc gggaaacctc ctcggattcc attgcccagc     240
tatctgtcac ttcatcaaaa ggacagtaga aaaggaaggt ggcacctaca aatgccatca     300
ttgcgataaa ggaaaggcta tcgttcaaga tgcctctgcc gacagtggtc ccaaagatgg     360
acccccaccc acgaggagca tcgtggaaaa agaagacgtt ccaaccacgt cttcaaagca     420
agtggattga tgtgatatct ccactgacgt aagggatgac gcacaatccc actatccttc     480
gcaagaccct tcctctatat aaggaagttc atttcatttg gagaggactc gacgagctca     540
tttctctatt acttcagcca taacaaaaga actcttttct cttcttatta aaccaggatc     600
catgatacac acgaatctga agaaaaagtt ctccttgttc attctcgtgt tccttctgtt     660
tgctgtcatt tgtgtttgga aaaagggatc tgattacgaa gctttgactc ttcaagctaa     720
ggaatttcaa atgccgaagt cccaagagaa agttgctaag ggtagaacaa aagagccgaa     780
agagaaactt cgtaactgcc cagaaacatc tacacttcta gttggtccgc ttcagatagt     840
gttttcaatg catgtggacc ttgaggacat aaggaaaagc aatccagatg taattgaggg     900
agggcactat cgaccaaaag attgtaacgc gttacaaaag gttgccatta tcatcccatt     960
cagaaacaga gatgaacacc taaagtactg gctctattac atgcatccta tcttgaagag    1020
acaacagttg gattacggtg tttacgtcat caatcaggat ggagataaga cgttcaatcg    1080
tgctaagttg ctcaatatcg gttatgtaga gagtttgaag gactatgcct atgactgttt    1140
tgtgttttct gatgtggact tgattcctat ggatgacaga aacacctatc gttgcttcaa    1200
```

-continued

```
tcagcctaga catctttctg cagctatgga caagtttggc tttggtttgc cttacaatca    1260
gttctttggt ggagtttcag cattgagtaa ggaacagttc ctgaagatta acggttttcc    1320
caacaattac tggggttggg gtggtgaaga tgatgacatc tacaacagga tagcatcaag    1380
agggatgtat atctcaagac cagataccct tatcggaaga tgcagaatga tcagacacaa    1440
tagagacgat aagaatgatc ctaatcccaa gagatttgac ctacttgctc atacaagaca    1500
gactatggat tctgatggca tcaatactct gagctataag gttgtcagta ctacaagatt    1560
ccctctttac acctacatta ctgtggatat cggtcttcca cattgagctt tgagaccgct    1620
agcaagcttg gacacgctga atcaccagt ctctctctac aaatctatct ctctctattt    1680
tctccataat aatgtgtgag tagttcccag ataagggaat taggggttcct ataggggttc    1740 gctcatgtgt tgagcatata agaaaccct agtatgtatt tgtatttgta aaatacttct    1800
atcaataaaa tttctaattc ctaaaaccaa aatccagtac taaaatccag atc           1853
```

<210> SEQ ID NO 2
<211> LENGTH: 1005
<212> TYPE: DNA
<213> ORGANISM: Artificial
<220> FEATURE:
<223> OTHER INFORMATION: DNA encoding Rn ST(CTS)-XtGalT(CAT)
<220> FEATURE:
<221> NAME/KEY: CDS
<222> LOCATION: (1)..(156)
<223> OTHER INFORMATION: CTS from rat alfa(2,6)-sialyltransferase
<220> FEATURE:
<221> NAME/KEY: CDS
<222> LOCATION: (157)..(1002)
<223> OTHER INFORMATION: catalytic domain of Xenopus beta(1,4) galactosyltransferase

<400> SEQUENCE: 2

```
atg ata cac acg aat ctg aag aaa aag ttc tcc ttg ttc att ctc gtg         48
Met Ile His Thr Asn Leu Lys Lys Lys Phe Ser Leu Phe Ile Leu Val
1               5                   10                  15 ttc ctt ctg ttt gct gtc att tgt gtt tgg aaa aag gga tct gat tac         96
Phe Leu Leu Phe Ala Val Ile Cys Val Trp Lys Lys Gly Ser Asp Tyr
            20                  25                  30 gaa gct ttg act ctt caa gct aag gaa ttt caa atg ccg aag tcc caa        144
Glu Ala Leu Thr Leu Gln Ala Lys Glu Phe Gln Met Pro Lys Ser Gln
        35                  40                  45 gag aaa gtt gct aag ggt aga aca aaa gag ccg aaa gag aaa ctt cgt        192
Glu Lys Val Ala Lys Gly Arg Thr Lys Glu Pro Lys Glu Lys Leu Arg
    50                  55                  60 aac tgc cca gaa aca tct aca ctt cta gtt ggt ccg ctt cag ata gtg        240
Asn Cys Pro Glu Thr Ser Thr Leu Leu Val Gly Pro Leu Gln Ile Val
65                  70                  75                  80 ttt tca atg cat gtg gac ctt gag gac ata agg aaa agc aat cca gat        288
Phe Ser Met His Val Asp Leu Glu Asp Ile Arg Lys Ser Asn Pro Asp
                85                  90                  95 gta att gag gga ggg cac tat cga cca aaa gat tgt aac gcg tta caa        336
Val Ile Glu Gly Gly His Tyr Arg Pro Lys Asp Cys Asn Ala Leu Gln
            100                 105                 110 aag gtt gcc att atc atc cca ttc aga aac aga gat gaa cac cta aag        384
Lys Val Ala Ile Ile Ile Pro Phe Arg Asn Arg Asp Glu His Leu Lys
        115                 120                 125 tac tgg ctc tat tac atg cat cct atc ttg aag aga caa cag ttg gat        432
Tyr Trp Leu Tyr Tyr Met His Pro Ile Leu Lys Arg Gln Gln Leu Asp
    130                 135                 140 tac ggt gtt tac gtc atc aat cag gat gga gat aag acg ttc aat cgt        480
Tyr Gly Val Tyr Val Ile Asn Gln Asp Gly Asp Lys Thr Phe Asn Arg
```

```
                                                                        528
gct aag ttg ctc aat atc ggt tat gta gag agt ttg aag gac tat gcc
Ala Lys Leu Leu Asn Ile Gly Tyr Val Glu Ser Leu Lys Asp Tyr Ala
            165                 170                 175

576
tat gac tgt ttt gtg ttt tct gat gtg gac ttg att cct atg gat gac
Tyr Asp Cys Phe Val Phe Ser Asp Val Asp Leu Ile Pro Met Asp Asp
        180                 185                 190

624
aga aac acc tat cgt tgc ttc aat cag cct aga cat ctt tct gca gct
Arg Asn Thr Tyr Arg Cys Phe Asn Gln Pro Arg His Leu Ser Ala Ala
                195                 200                 205

672
atg gac aag ttt ggc ttt ggt ttg cct tac aat cag ttc ttt ggt gga
Met Asp Lys Phe Gly Phe Gly Leu Pro Tyr Asn Gln Phe Phe Gly Gly
    210                 215                 220

720
gtt tca gca ttg agt aag gaa cag ttc ctg aag att aac ggt ttt ccc
Val Ser Ala Leu Ser Lys Glu Gln Phe Leu Lys Ile Asn Gly Phe Pro
225                 230                 235                 240

768
aac aat tac tgg ggt tgg ggt ggt gaa gat gat gac atc tac aac agg
Asn Asn Tyr Trp Gly Trp Gly Gly Glu Asp Asp Asp Ile Tyr Asn Arg
                245                 250                 255

816
ata gca tca aga ggg atg tat atc tca aga cca gat acc ctt atc gga
Ile Ala Ser Arg Gly Met Tyr Ile Ser Arg Pro Asp Thr Leu Ile Gly
            260                 265                 270

864
aga tgc aga atg atc aga cac aat aga gac gat aag aat gat cct aat
Arg Cys Arg Met Ile Arg His Asn Arg Asp Asp Lys Asn Asp Pro Asn
        275                 280                 285

912
ccc aag aga ttt gac cta ctt gct cat aca aga cag act atg gat tct
Pro Lys Arg Phe Asp Leu Leu Ala His Thr Arg Gln Thr Met Asp Ser
    290                 295                 300

960
gat ggc atc aat act ctg agc tat aag gtt gtc agt act aca aga ttc
Asp Gly Ile Asn Thr Leu Ser Tyr Lys Val Val Ser Thr Thr Arg Phe
305                 310                 315                 320

1005
cct ctt tac acc tac att act gtg gat atc ggt ctt cca cat tga
Pro Leu Tyr Thr Tyr Ile Thr Val Asp Ile Gly Leu Pro His
                325                 330
```

<210> SEQ ID NO 3
<211> LENGTH: 334
<212> TYPE: PRT
<213> ORGANISM: Artificial
<220> FEATURE:
<223> OTHER INFORMATION: Synthetic Construct

<400> SEQUENCE: 3

```
Met Ile His Thr Asn Leu Lys Lys Lys Phe Ser Leu Phe Ile Leu Val
1               5                   10                  15

Phe Leu Leu Phe Ala Val Ile Cys Val Trp Lys Lys Gly Ser Asp Tyr
            20                  25                  30

Glu Ala Leu Thr Leu Gln Ala Lys Glu Phe Gln Met Pro Lys Ser Gln
        35                  40                  45

Glu Lys Val Ala Lys Gly Arg Thr Lys Glu Pro Lys Glu Lys Leu Arg
    50                  55                  60

Asn Cys Pro Glu Thr Ser Thr Leu Leu Val Gly Pro Leu Gln Ile Val
65                  70                  75                  80

Phe Ser Met His Val Asp Leu Glu Asp Ile Arg Lys Ser Asn Pro Asp
                85                  90                  95

Val Ile Glu Gly Gly His Tyr Arg Pro Lys Asp Cys Asn Ala Leu Gln
            100                 105                 110

Lys Val Ala Ile Ile Ile Pro Phe Arg Asn Arg Asp Glu His Leu Lys
```

Tyr Gly Val Tyr Val Ile Asn Gln Asp Gly Asp Lys Thr Phe Asn Arg
145                 150                 155                 160

```
                        115                 120                 125
Tyr Trp Leu Tyr Tyr Met His Pro Ile Leu Lys Arg Gln Gln Leu Asp
    130                 135                 140

Tyr Gly Val Tyr Val Ile Asn Gln Asp Gly Asp Lys Thr Phe Asn Arg
145                 150                 155                 160

Ala Lys Leu Leu Asn Ile Gly Tyr Val Glu Ser Leu Lys Asp Tyr Ala
                165                 170                 175

Tyr Asp Cys Phe Val Phe Ser Asp Val Asp Leu Ile Pro Met Asp Asp
            180                 185                 190

Arg Asn Thr Tyr Arg Cys Phe Asn Gln Pro Arg His Leu Ser Ala Ala
        195                 200                 205

Met Asp Lys Phe Gly Phe Gly Leu Pro Tyr Asn Gln Phe Phe Gly Gly
    210                 215                 220

Val Ser Ala Leu Ser Lys Glu Gln Phe Leu Lys Ile Asn Gly Phe Pro
225                 230                 235                 240

Asn Asn Tyr Trp Gly Trp Gly Gly Glu Asp Asp Asp Ile Tyr Asn Arg
                245                 250                 255

Ile Ala Ser Arg Gly Met Tyr Ile Ser Arg Pro Asp Thr Leu Ile Gly
            260                 265                 270

Arg Cys Arg Met Ile Arg His Asn Arg Asp Asp Lys Asn Asp Pro Asn
        275                 280                 285

Pro Lys Arg Phe Asp Leu Leu Ala His Thr Arg Gln Thr Met Asp Ser
    290                 295                 300

Asp Gly Ile Asn Thr Leu Ser Tyr Lys Val Val Ser Thr Thr Arg Phe
305                 310                 315                 320

Pro Leu Tyr Thr Tyr Ile Thr Val Asp Ile Gly Leu Pro His
                325                 330

<210> SEQ ID NO 4
<211> LENGTH: 1952
<212> TYPE: DNA
<213> ORGANISM: Artificial
<220> FEATURE:
<223> OTHER INFORMATION: Expression cassette for RN ST(CTS)-XtGalT(SCAT)
<220> FEATURE:
<221> NAME/KEY: promoter
<222> LOCATION: (1)..(528)
<223> OTHER INFORMATION: P35S2: Promoter region from CaMV35S gene
<220> FEATURE:
<221> NAME/KEY: 5'UTR
<222> LOCATION: (535)..(595)
<223> OTHER INFORMATION: 5'cab22L: untranslated leader sequence of
      cab22L gene from petunia
<220> FEATURE:
<221> NAME/KEY: misc_feature
<222> LOCATION: (602)..(757)
<223> OTHER INFORMATION: CTS of rat alfa(2,6)-sialyltransferase
<220> FEATURE:
<221> NAME/KEY: misc_feature
<222> LOCATION: (758)..(1705)
<223> OTHER INFORMATION: Stem region and catalytic domain of Xenopus
      beta(1,4)-galactosyltransferase
<220> FEATURE:
<221> NAME/KEY: terminator
<222> LOCATION: (1729)..(1952)
<223> OTHER INFORMATION: 3'35S: 3' untranslated region from the CaMV35S
      gene

<400> SEQUENCE: 4
catggagtca aaaattcaga tcgaggatct aacagaactc gccgtgaaga ctggcgaaca        60
gttcatacag agtcttttac gactcaatga caagaagaaa atcttcgtca acatggtgga       120
gcacgacact ctcgtctact ccaagaatat caaagataca gtctcagaag accaaagggc       180
```

```
tattgagact tttcaacaaa gggtaatatc gggaaacctc ctcggattcc attgcccagc    240
tatctgtcac ttcatcaaaa ggacagtaga aaaggaaggt ggcacctaca aatgccatca    300
ttgcgataaa ggaaaggcta tcgttcaaga tgcctctgcc gacagtggtc ccaaagatgg    360 accccaccc acgaggagca tcgtggaaaa agaagacgtt ccaaccacgt cttcaaagca    420
agtggattga tgtgatatct ccactgacgt aagggatgac gcacaatccc actatccttc    480
gcaagaccct tcctctatat aaggaagttc atttcatttg agaggactc gacgagctca    540 tttctctatt acttcagcca taacaaaaga actcttttct cttcttatta aaccaggatc    600
catgattcac acaaatttaa aaaaaaaatt tagccttttt attctcgtat ttttactgtt    660
tgctgtcatc tgcgtttgga agaaagggtc tgattatgaa gctctaaccc tccaggctaa    720
agagtttcaa atgccaaaat cccaggagaa agtagcttttt ggaatcttac aattcttccg    780
ccaaaatcaa cagtctcaac tggcatataa acaaaactat acgattagca acgccactat    840
gcgagctata agcacaaaag gacggactaa ggaaccaaag gagaaactgc ggaattgtcc    900
agaaacaagt acacttttgg ttgggccgct tcaaattgtt ttctcaatgc acgtggatct    960
tgaggatata cgaaaaagta atccggatgt gatagaggga ggccattata ggccgaaaga   1020
ctgtaacgcg ttacaaaagg ttgccattat catcccattc agaaacagag atgaacacct   1080
aaagtactgg ctctattaca tgcatcctat cttgaagaga caacagttgg attacggtgt   1140
ttacgtcatc aatcaggatg gagataagac gttcaatcgt gctaagttgc tcaatatcgg   1200
ttatgtagag agtttgaagg actatgccta tgactgtttt gtgttttctg atgtggactt   1260
gattcctatg gatgacagaa acacctatcg ttgcttcaat cagcctagac atctttctgc   1320
agctatggac aagtttggct ttggtttgcc ttacaatcag ttctttggtg gagtttcagc   1380
attgagtaag gaacagttcc tgaagattaa cggttttccc aacaattact ggggttgggg   1440
tggtgaagat gatgacatct acaacaggat agcatcaaga gggatgtata tctcaagacc   1500 agatacccctt atcggaagat gcagaatgat cagacacaat agagacgata gaatgatcc   1560 taatcccaag agatttgacc tacttgctca tacaagacag actatggatt ctgatggcat   1620
caatactctg agctataagg ttgtcagtac tacaagattc cctctttaca cctacattac   1680
tgtggatatc ggtcttccac attgagcttt gagaccgcta gcaagcttgg acacgctgaa   1740
atcaccagtc tctctctaca aatctatctc tctctatttt ctccataata atgtgtgagt   1800 agttccaga taagggaatt aggggttccta tagggtttcg ctcatgtgtt gagcatataa   1860 gaaacccctta gtatgtattt gtatttgtaa aatacttcta tcaataaaat ttctaattcc   1920
taaaaccaaa atccagtact aaaatccaga tc                                  1952
```

<210> SEQ ID NO 5
<211> LENGTH: 1104
<212> TYPE: DNA
<213> ORGANISM: Artificial
<220> FEATURE:
<223> OTHER INFORMATION: DNA encoding Rn ST(CTS)-XtGalT(SCAT)
<220> FEATURE:
<221> NAME/KEY: CDS
<222> LOCATION: (1)..(156)
<223> OTHER INFORMATION: CTS from rat alfa(2,6)-sialyltransferase
<220> FEATURE:
<221> NAME/KEY: CDS
<222> LOCATION: (157)..(1101)
<223> OTHER INFORMATION: Stem region + catalytic domain of Xenopus beta(1,4)-galactosyltransferase

<400> SEQUENCE: 5

```
atg att cac aca aat tta aaa aaa aaa ttt agc ctt ttt att ctc gta      48
Met Ile His Thr Asn Leu Lys Lys Lys Phe Ser Leu Phe Ile Leu Val
1               5                   10                  15 ttt tta ctg ttt gct gtc atc tgc gtt tgg aag aaa ggg tct gat tat      96
Phe Leu Leu Phe Ala Val Ile Cys Val Trp Lys Lys Gly Ser Asp Tyr
            20                  25                  30 gaa gct cta acc ctc cag gct aaa gag ttt caa atg cca aaa tcc cag     144
Glu Ala Leu Thr Leu Gln Ala Lys Glu Phe Gln Met Pro Lys Ser Gln
        35                  40                  45 gag aaa gta gct ttt gga atc tta caa ttc ttc cgc caa aat caa cag     192
Glu Lys Val Ala Phe Gly Ile Leu Gln Phe Phe Arg Gln Asn Gln Gln
    50                  55                  60 tct caa ctg gca tat aaa caa aac tat acg att agc aac gcc act atg     240
Ser Gln Leu Ala Tyr Lys Gln Asn Tyr Thr Ile Ser Asn Ala Thr Met
65                  70                  75                  80 cga gct ata agc aca aaa gga cgg act aag gaa cca aag gag aaa ctg     288
Arg Ala Ile Ser Thr Lys Gly Arg Thr Lys Glu Pro Lys Glu Lys Leu
                85                  90                  95 cgg aat tgt cca gaa aca agt aca ctt ttg gtt ggg ccg ctt caa att     336
Arg Asn Cys Pro Glu Thr Ser Thr Leu Leu Val Gly Pro Leu Gln Ile
            100                 105                 110 gtt ttc tca atg cac gtg gat ctt gag gat ata cga aaa agt aat ccg     384
Val Phe Ser Met His Val Asp Leu Glu Asp Ile Arg Lys Ser Asn Pro
        115                 120                 125 gat gtg ata gag gga ggc cat tat agg ccg aaa gac tgt aac gcg tta     432
Asp Val Ile Glu Gly Gly His Tyr Arg Pro Lys Asp Cys Asn Ala Leu
    130                 135                 140 caa aag gtt gcc att atc atc cca ttc aga aac aga gat gaa cac cta     480
Gln Lys Val Ala Ile Ile Ile Pro Phe Arg Asn Arg Asp Glu His Leu
145                 150                 155                 160 aag tac tgg ctc tat tac atg cat cct atc ttg aag aga caa cag ttg     528
Lys Tyr Trp Leu Tyr Tyr Met His Pro Ile Leu Lys Arg Gln Gln Leu
                165                 170                 175 gat tac ggt gtt tac gtc atc aat cag gat gga gat aag acg ttc aat     576
Asp Tyr Gly Val Tyr Val Ile Asn Gln Asp Gly Asp Lys Thr Phe Asn
            180                 185                 190 cgt gct aag ttg ctc aat atc ggt tat gta gag agt ttg aag gac tat     624
Arg Ala Lys Leu Leu Asn Ile Gly Tyr Val Glu Ser Leu Lys Asp Tyr
        195                 200                 205 gcc tat gac tgt ttt gtg ttt tct gat gtg gac ttg att cct atg gat     672
Ala Tyr Asp Cys Phe Val Phe Ser Asp Val Asp Leu Ile Pro Met Asp
    210                 215                 220 gac aga aac acc tat cgt tgc ttc aat cag cct aga cat ctt tct gca     720
Asp Arg Asn Thr Tyr Arg Cys Phe Asn Gln Pro Arg His Leu Ser Ala
225                 230                 235                 240 gct atg gac aag ttt ggc ttt ggt ttg cct tac aat cag ttc ttt ggt     768
Ala Met Asp Lys Phe Gly Phe Gly Leu Pro Tyr Asn Gln Phe Phe Gly
                245                 250                 255 gga gtt tca gca ttg agt aag gaa cag ttc ctg aag att aac ggt ttt     816
Gly Val Ser Ala Leu Ser Lys Glu Gln Phe Leu Lys Ile Asn Gly Phe
            260                 265                 270 ccc aac aat tac tgg ggt tgg ggt ggt gaa gat gat gac atc tac aac     864
Pro Asn Asn Tyr Trp Gly Trp Gly Gly Glu Asp Asp Asp Ile Tyr Asn
        275                 280                 285 agg ata gca tca aga ggg atg tat atc tca aga cca gat acc ctt atc     912
Arg Ile Ala Ser Arg Gly Met Tyr Ile Ser Arg Pro Asp Thr Leu Ile
    290                 295                 300 gga aga tgc aga atg atc aga cac aat aga gac gat aag aat gat cct     960
Gly Arg Cys Arg Met Ile Arg His Asn Arg Asp Asp Lys Asn Asp Pro
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 305 |     |     |     | 310 |     |     |     | 315 |     |     |     | 320 |     |      |
| aat | ccc | aag | aga | ttt | gac | cta | ctt | gct | cat | aca | aga | cag | act | atg | gat | 1008 |
| Asn | Pro | Lys | Arg | Phe | Asp | Leu | Leu | Ala | His | Thr | Arg | Gln | Thr | Met | Asp |      |
|     |     | 325 |     |     |     |     |     |     | 330 |     |     |     |     | 335 |     |      |
| tct | gat | ggc | atc | aat | act | ctg | agc | tat | aag | gtt | gtc | agt | act | aca | aga | 1056 |
| Ser | Asp | Gly | Ile | Asn | Thr | Leu | Ser | Tyr | Lys | Val | Val | Ser | Thr | Thr | Arg |      |
|     |     | 340 |     |     |     |     |     | 345 |     |     |     |     | 350 |     |     |      |
| ttc | cct | ctt | tac | acc | tac | att | act | gtg | gat | atc | ggt | ctt | cca | cat | tga | 1104 |
| Phe | Pro | Leu | Tyr | Thr | Tyr | Ile | Thr | Val | Asp | Ile | Gly | Leu | Pro | His |     |      |
|     |     | 355 |     |     |     |     |     | 360 |     |     |     |     | 365 |     |     |      |

<210> SEQ ID NO 6
<211> LENGTH: 367
<212> TYPE: PRT
<213> ORGANISM: Artificial
<220> FEATURE:
<223> OTHER INFORMATION: Synthetic Construct

<400> SEQUENCE: 6

Met Ile His Thr Asn Leu Lys Lys Phe Ser Leu Phe Ile Leu Val
1               5                   10                  15

Phe Leu Leu Phe Ala Val Ile Cys Val Trp Lys Lys Gly Ser Asp Tyr
        20                  25                  30

Glu Ala Leu Thr Leu Gln Ala Lys Glu Phe Gln Met Pro Lys Ser Gln
        35                  40                  45

Glu Lys Val Ala Phe Gly Ile Leu Gln Phe Phe Arg Gln Asn Gln Gln
    50                  55                  60

Ser Gln Leu Ala Tyr Lys Gln Asn Tyr Thr Ile Ser Asn Ala Thr Met
65              70                  75                  80

Arg Ala Ile Ser Thr Lys Gly Arg Thr Lys Glu Pro Lys Glu Lys Leu
                85                  90                  95

Arg Asn Cys Pro Glu Thr Ser Thr Leu Leu Val Gly Pro Leu Gln Ile
            100                 105                 110

Val Phe Ser Met His Val Asp Leu Glu Asp Ile Arg Lys Ser Asn Pro
        115                 120                 125

Asp Val Ile Glu Gly Gly His Tyr Arg Pro Lys Asp Cys Asn Ala Leu
130                 135                 140

Gln Lys Val Ala Ile Ile Ile Pro Phe Arg Asn Arg Asp Glu His Leu
145                 150                 155                 160

Lys Tyr Trp Leu Tyr Tyr Met His Pro Ile Leu Lys Arg Gln Gln Leu
                165                 170                 175

Asp Tyr Gly Val Tyr Val Ile Asn Gln Asp Gly Asp Lys Thr Phe Asn
            180                 185                 190

Arg Ala Lys Leu Leu Asn Ile Gly Tyr Val Glu Ser Leu Lys Asp Tyr
        195                 200                 205

Ala Tyr Asp Cys Phe Val Phe Ser Asp Val Asp Leu Ile Pro Met Asp
    210                 215                 220

Asp Arg Asn Thr Tyr Arg Cys Phe Asn Gln Pro Arg His Leu Ser Ala
225                 230                 235                 240

Ala Met Asp Lys Phe Gly Phe Gly Leu Pro Tyr Asn Gln Phe Phe Gly
                245                 250                 255

Gly Val Ser Ala Leu Ser Lys Glu Gln Phe Leu Lys Ile Asn Gly Phe
            260                 265                 270

Pro Asn Asn Tyr Trp Gly Trp Gly Gly Glu Asp Asp Asp Ile Tyr Asn
        275                 280                 285

```
Arg Ile Ala Ser Arg Gly Met Tyr Ile Ser Arg Pro Asp Thr Leu Ile
            290                 295                 300

Gly Arg Cys Arg Met Ile Arg His Asn Arg Asp Lys Asn Asp Pro
305                 310                 315                 320

Asn Pro Lys Arg Phe Asp Leu Leu Ala His Thr Arg Gln Thr Met Asp
                325                 330                 335

Ser Asp Gly Ile Asn Thr Leu Ser Tyr Lys Val Val Ser Thr Thr Arg
            340                 345                 350

Phe Pro Leu Tyr Thr Tyr Ile Thr Val Asp Ile Gly Leu Pro His
                355                 360                 365

<210> SEQ ID NO 7
<211> LENGTH: 52
<212> TYPE: PRT
<213> ORGANISM: Rattus norvegicus

<400> SEQUENCE: 7

Met Ile His Thr Asn Leu Lys Lys Lys Phe Ser Leu Phe Ile Leu Val
1               5                   10                  15

Phe Leu Leu Phe Ala Val Ile Cys Val Trp Lys Lys Gly Ser Asp Tyr
            20                  25                  30

Glu Ala Leu Thr Leu Gln Ala Lys Glu Phe Gln Met Pro Lys Ser Gln
        35                  40                  45

Glu Lys Val Ala
    50

<210> SEQ ID NO 8
<211> LENGTH: 80
<212> TYPE: PRT
<213> ORGANISM: Xenopus tropicalis

<400> SEQUENCE: 8

Met Lys Glu Pro Gln Leu Pro Val Ser Asn Leu Thr Ala Ala Leu Pro
1               5                   10                  15

Gly Ala Ser Leu Gln Lys Ala Cys Lys Phe Val Val Val Phe Cys Ser
            20                  25                  30

Leu His Phe Cys Val Val Leu Ile Tyr Tyr Leu Ser Gly Ala Asp Phe
        35                  40                  45

Gly Ile Leu Gln Phe Phe Arg Gln Asn Gln Gln Ser Gln Leu Ala Tyr
    50                  55                  60

Lys Gln Asn Tyr Thr Ile Ser Asn Ala Thr Met Arg Ala Ile Ser Thr
65                  70                  75                  80

<210> SEQ ID NO 9
<211> LENGTH: 26
<212> TYPE: PRT
<213> ORGANISM: Rattus norvegicus

<400> SEQUENCE: 9

Lys Lys Gly Ser Asp Tyr Glu Ala Leu Thr Leu Gln Ala Lys Glu Phe
1               5                   10                  15

Gln Met Pro Lys Ser Gln Glu Lys Val Ala
            20                  25

<210> SEQ ID NO 10
<211> LENGTH: 33
<212> TYPE: PRT
<213> ORGANISM: Xenopus tropicalis
```

```
<400> SEQUENCE: 10

Phe Gly Ile Leu Gln Phe Phe Arg Gln Asn Gln Gln Ser Gln Leu Ala
1               5                   10                  15

Tyr Lys Gln Asn Tyr Thr Ile Ser Asn Ala Thr Met Arg Ala Ile Ser
                20                  25                  30

Thr

<210> SEQ ID NO 11
<211> LENGTH: 282
<212> TYPE: PRT
<213> ORGANISM: Xenopus tropicalis

<400> SEQUENCE: 11

Lys Gly Arg Thr Lys Glu Pro Lys Glu Lys Leu Arg Asn Cys Pro Glu
1               5                   10                  15

Thr Ser Thr Leu Leu Val Gly Pro Leu Gln Ile Val Phe Ser Met His
                20                  25                  30

Val Asp Leu Glu Asp Ile Arg Lys Ser Asn Pro Asp Val Ile Glu Gly
                35                  40                  45

Gly His Tyr Arg Pro Lys Asp Cys Asn Ala Leu Gln Lys Val Ala Ile
            50                  55                  60

Ile Ile Pro Phe Arg Asn Arg Asp Glu His Leu Lys Tyr Trp Leu Tyr
65                  70                  75                  80

Tyr Met His Pro Ile Leu Lys Arg Gln Gln Leu Asp Tyr Gly Val Tyr
                85                  90                  95

Val Ile Asn Gln Asp Gly Asp Lys Thr Phe Asn Arg Ala Lys Leu Leu
                100                 105                 110

Asn Ile Gly Tyr Val Glu Ser Leu Lys Asp Tyr Ala Tyr Asp Cys Phe
            115                 120                 125

Val Phe Ser Asp Val Asp Leu Ile Pro Met Asp Asp Arg Asn Thr Tyr
            130                 135                 140

Arg Cys Phe Asn Gln Pro Arg His Leu Ser Ala Ala Met Asp Lys Phe
145                 150                 155                 160

Gly Phe Gly Leu Pro Tyr Asn Gln Phe Phe Gly Gly Val Ser Ala Leu
                165                 170                 175

Ser Lys Glu Gln Phe Leu Lys Ile Asn Gly Phe Pro Asn Asn Tyr Trp
            180                 185                 190

Gly Trp Gly Gly Glu Asp Asp Ile Tyr Asn Arg Ile Ala Ser Arg
            195                 200                 205

Gly Met Tyr Ile Ser Arg Pro Asp Thr Leu Ile Gly Arg Cys Arg Met
            210                 215                 220

Ile Arg His Asn Arg Asp Asp Lys Asn Asp Pro Asn Pro Lys Arg Phe
225                 230                 235                 240

Asp Leu Leu Ala His Thr Arg Gln Thr Met Asp Ser Asp Gly Ile Asn
                245                 250                 255

Thr Leu Ser Tyr Lys Val Val Ser Thr Thr Arg Phe Pro Leu Tyr Thr
                260                 265                 270

Tyr Ile Thr Val Asp Ile Gly Leu Pro His
            275                 280
```